US006253764B1

(12) United States Patent
Calluaud

(10) Patent No.: US 6,253,764 B1
(45) Date of Patent: Jul. 3, 2001

(54) CONTROL OF DELIVERY PRESSURE IN CPAP TREATMENT OR ASSISTED RESPIRATION

(75) Inventor: Michel Calluaud, Bayview (AU)

(73) Assignee: ResMed, Ltd., New South Wales (AU)

( * ) Notice: Subject to any disclaimer, the term of this patent is extended or adjusted under 35 U.S.C. 154(b) by 0 days.

(21) Appl. No.: 08/851,940

(22) Filed: May 7, 1997

(30) Foreign Application Priority Data

May 8, 1996 (AU) .................................................. PN9735

(51) Int. Cl.$^7$ .................................................. A61M 16/00

(52) U.S. Cl. ............................... 128/204.18; 128/204.26; 128/205.24

(58) Field of Search ........................ 128/204.18, 204.21, 128/204.23, 204.26, 205.24

(56) References Cited

U.S. PATENT DOCUMENTS

| Re. 35,295 | 7/1996 | Estes et al. . |
| Re. 35,339 | 10/1996 | Rapoport . |
| 2,904,033 | 9/1959 | Shane . |
| 3,099,985 | 8/1963 | Wilson et al. . |
| 3,559,638 | 2/1971 | Potter . |
| 3,595,228 | 7/1971 | Simon et al. . |

(List continued on next page.)

FOREIGN PATENT DOCUMENTS

| 59270/90 | 12/1990 | (AU) . |
| 62221/90 | 3/1991 | (AU) . |
| 33877/93 | 4/1993 | (AU) . |
| 38508/93 | 7/1993 | (AU) . |
| 48748/93 | 12/1993 | (AU) . |
| 52628/93 | 7/1994 | (AU) . |

(List continued on next page.)

OTHER PUBLICATIONS

Mark Kantrowitz, Erik Horskotte and Cliff Joslyn; "Answers to Frequently Asked Questions about Fuzzy Logic and Fuzzy Expert Systems" Version 1.24 last modified Feb. 20, 1996.
New! Breas PV 100 CPAP First Class Quality and Function. At the right Price; Jul. 4, 1998, pp 1–2.
PV 101 Bi Level CPAP and PV 102 Bi–Level Time; pp 1–3. Prodigy Medical Supplies Co. Ltd.; CPAP.
Puritan Bennett; Companion 318 Nasal CPAP System; 5/93.
Nellcor Puritan Bennett; Announcing the Goodnight 314 and GoodKnight 318 Nasal CPAP Systems.

(List continued on next page.)

Primary Examiner—Aaron J. Lewis
(74) Attorney, Agent, or Firm—Pillsbury Winthrop LLP

(57) ABSTRACT

A pressure control apparatus (10) for CPAP treatment or assisted respiration. The apparatus (10) includes an inlet chamber (20) for connection to a primary supply of air or other breathable gas at a pressure at or above a maximum treatment pressure, an outlet chamber (30) for communication with a mask (14) or the like, a diaphragm (32) for communication with a portion of the outlet chamber (30), means (22) to provide a predetermined force to the diaphragm (32), a first valve means (36) operable to open a flow path between the outlet chamber (30) and the inlet chamber (20) in response to deflection of the diaphragm (32) in a first direction and a second valve means (40) operable to provide an exhaust path from the outlet chamber (30) to atmosphere in response to deflection of the diaphragm (32) in a second direction opposite to the first direction. When the pressure of gas in the outlet chamber (30) produces a force on the diaphragm (32) below the predetermined force the force differential on the diaphragm (32) causes it to deflect in the first direction and cause the first valve means (36) to open and to cause an equilibrating flow of gas from the inlet chamber (20). When the pressure of gas in the outlet chamber (30) produces a force on the diaphragm (32) above the predetermined force the force differential on the diaphragm (32) causes it to deflect in the second direction and cause the second valve means (40) to open.

13 Claims, 14 Drawing Sheets

U.S. PATENT DOCUMENTS

| | | |
|---|---|---|
| 3,611,801 | 10/1971 | Paine et al. . |
| 3,741,208 | 6/1973 | Jonsson et al. . |
| 3,783,893 | 1/1974 | Davison . |
| 3,802,417 | 4/1974 | Lang . |
| 3,817,246 | 6/1974 | Weigl . |
| 3,834,383 | 9/1974 | Weigl et al. . |
| 3,840,006 | 10/1974 | Buck et al. . |
| 3,859,995 | 1/1975 | Colston . |
| 3,863,630 | 2/1975 | Cavallo . |
| 3,882,847 | 5/1975 | Jacobs . |
| 3,903,875 | 9/1975 | Hughes . |
| 3,914,994 | 10/1975 | Banner . |
| 3,932,054 | 1/1976 | McKelvey . |
| 3,961,627 | 6/1976 | Ernst et al. . |
| 3,972,327 | 8/1976 | Ernst et al. . |
| 3,985,467 | 10/1976 | Lefferson . |
| 3,989,037 | 11/1976 | Franetki . |
| 3,992,598 | 11/1976 | Welsh et al. . |
| 3,995,661 | 12/1976 | Van Fossen . |
| 4,006,634 | 2/1977 | Billette et al. . |
| 4,083,245 | 4/1978 | Osborn . |
| 4,109,749 | 8/1978 | Sweet . |
| 4,231,365 | 11/1980 | Scarberry . |
| 4,239,039 | 12/1980 | Thompson . |
| 4,249,527 | 2/1981 | Ko et al. . |
| 4,262,667 | 4/1981 | Grant . |
| 4,281,651 | 8/1981 | Cox . |
| 4,301,833 | 11/1981 | Donald, III . |
| 4,312,235 | 1/1982 | Daigle . |
| 4,322,594 | 3/1982 | Brisson . |
| 4,381,788 | 5/1983 | Douglas . |
| 4,387,722 | 6/1983 | Kearns . |
| 4,393,869 | 7/1983 | Boyarsky . |
| 4,396,034 | 8/1983 | Cherniak . |
| 4,414,982 | 11/1983 | Durkan . |
| 4,430,995 | 2/1984 | Hilton . |
| 4,433,693 | 2/1984 | Hochstein . |
| 4,448,058 | 5/1984 | Jaffe et al. . |
| 4,449,525 | 5/1984 | White et al. . |
| 4,499,914 | 2/1985 | Schebler . |
| 4,501,273 | 2/1985 | McGinnis . |
| 4,506,666 | 3/1985 | Durkan . |
| 4,527,557 | 7/1985 | DeVries et al. . |
| 4,530,334 | 7/1985 | Pagdin . |
| 4,537,190 | 8/1985 | Caillot et al. . |
| 4,550,615 | 11/1985 | Grant . |
| 4,550,726 | 11/1985 | McEwen . |
| 4,558,710 | 12/1985 | Eichler . |
| 4,559,940 | 12/1985 | McGinnis . |
| 4,570,631 | 2/1986 | Durkan . |
| 4,579,114 | 4/1986 | Gray et al. . |
| 4,580,575 | 4/1986 | Birnbaum et al. . |
| 4,584,996 | 4/1986 | Blum . |
| 4,595,016 | 6/1986 | Fertig et al. . |
| 4,602,644 | 7/1986 | DiBenedetto et al. . |
| 4,612,928 | 9/1986 | Tiep et al. . |
| 4,630,614 | 12/1986 | Atlas . |
| 4,637,385 | 1/1987 | Rusx . |
| 4,637,386 | 1/1987 | Baum . |
| 4,648,396 | 3/1987 | Raemer . |
| 4,648,407 | 3/1987 | Sackner . |
| 4,655,213 | 4/1987 | Rapoport et al. . |
| 4,660,555 | 4/1987 | Payton . |
| 4,677,975 | 7/1987 | Edgar et al. . |
| 4,686,974 | 8/1987 | Sato et al. . |
| 4,686,975 | 8/1987 | Naimon et al. . |
| 4,686,999 | 8/1987 | Snyder et al. . |
| 4,738,266 | 4/1988 | Thatcher . |
| 4,773,411 | 9/1988 | Downs . |
| 4,777,963 | 10/1988 | McKenna . |
| 4,795,314 | 1/1989 | Prybella et al. . |
| 4,802,485 | 2/1989 | Bowers et al. . |
| 4,803,471 | 2/1989 | Rowland . |
| 4,819,629 | 4/1989 | Jonson . |
| 4,823,788 | 4/1989 | Smith et al. . |
| 4,825,802 | 5/1989 | Le Bec . |
| 4,827,922 | 5/1989 | Champain et al. . |
| 4,827,964 | 5/1989 | Guido et al. . |
| 4,838,257 | 6/1989 | Hatch . |
| 4,838,258 | 6/1989 | Dryden et al. . |
| 4,844,085 | 7/1989 | Gattinoni . |
| 4,856,506 | 8/1989 | Jinotti . |
| 4,860,766 | 8/1989 | Sackner . |
| 4,870,960 | 10/1989 | Hradek . |
| 4,870,963 | 10/1989 | Carter . |
| 4,913,401 | 4/1990 | Handke . |
| 4,915,103 | 4/1990 | Visveshwara et al. . |
| 4,938,210 | 7/1990 | Shene . |
| 4,938,212 | 7/1990 | Snook et al. . |
| 4,944,310 | 7/1990 | Sullivan . |
| 4,957,107 | 9/1990 | Sipin . |
| 4,960,118 | 10/1990 | Pennock . |
| 4,971,050 | 11/1990 | Bartos . |
| 4,971,065 | 11/1990 | Pearce . |
| 4,972,842 | 11/1990 | Korten et al. . |
| 4,982,738 | 1/1991 | Griebel . |
| 5,002,050 | 3/1991 | McGinnis . |
| 5,009,635 | 4/1991 | Scarberry . |
| 5,024,219 | 6/1991 | Dietz . |
| 5,042,470 | 8/1991 | Kanesaka . |
| 5,046,491 | 9/1991 | Derrick . |
| 5,048,515 | 9/1991 | Sanso . |
| 5,052,400 | 10/1991 | Dietz . |
| 5,063,922 | 11/1991 | Hakkinen . |
| 5,063,925 * | 11/1991 | Frank et al. .................... 128/204.18 |
| 5,065,746 * | 11/1991 | Steen .............................. 128/204.18 |
| 5,065,756 | 11/1991 | Rapoport . |
| 5,067,487 | 11/1991 | Bauman . |
| 5,069,222 | 12/1991 | McDonald, Jr. . |
| 5,099,836 | 3/1992 | Rowland et al. . |
| 5,105,354 | 4/1992 | Nishimura . |
| 5,107,830 | 4/1992 | Younes . |
| 5,117,819 | 6/1992 | Servidio et al. . |
| 5,129,390 | 7/1992 | Chopin et al. . |
| 5,134,995 | 8/1992 | Gruenke et al. . |
| 5,148,802 | 9/1992 | Sanders et al. . |
| 5,161,525 | 11/1992 | Kimm et al. . |
| 5,161,541 | 11/1992 | Bowman et al. . |
| 5,170,798 | 12/1992 | Riker . |
| 5,174,287 | 12/1992 | Kallok et al. . |
| 5,178,138 | 1/1993 | Walstrom et al. . |
| 5,183,983 | 2/1993 | Knop . |
| 5,190,048 | 3/1993 | Wilkinson . |
| 5,195,528 | 3/1993 | Hok . |
| 5,199,424 | 4/1993 | Sullivan et al. . |
| 5,203,343 | 4/1993 | Axe et al. . |
| 5,222,478 | 6/1993 | Scarberry et al. . |
| 5,230,330 | 7/1993 | Price . |
| 5,231,979 | 8/1993 | Rose et al. . |
| 5,231,983 | 8/1993 | Matson et al. . |
| 5,239,995 | 8/1993 | Estes et al. . |
| 5,245,995 | 9/1993 | Sullivan et al. . |
| 5,255,687 | 10/1993 | McKenna . |
| 5,259,373 | 11/1993 | Gruenke et al. . |
| 5,271,391 | 12/1993 | Graves . |
| 5,280,784 | 1/1994 | Kohler . |
| 5,293,864 | 3/1994 | McFadden . |
| 5,303,700 | 4/1994 | Weismann et al. . |
| 5,305,787 | 4/1994 | Thygesen . |
| 5,311,875 | 5/1994 | Stasz . |
| 5,313,937 | 5/1994 | Zdrojkowski . |

| | | | | | | |
|---|---|---|---|---|---|---|
| 5,322,057 | 6/1994 | Raabe et al. . | | 0 066 451 A1 | 12/1982 | (EP) . |
| 5,335,654 | 8/1994 | Rapoport . | | 0 088 761 | 9/1983 | (EP) . |
| 5,343,878 | 9/1994 | Scarberry et al. . | | 0 164 500 A2 | 3/1985 | (EP) . |
| 5,353,788 | 10/1994 | Miles . | | 0 171 321 A1 | 2/1986 | (EP) . |
| 5,360,008 | 11/1994 | Campbell, Jr. . | | 0 185 980 | 7/1986 | (EP) . |
| 5,388,571 | 2/1995 | Roberts et al. . | | 0 236 850 A2 | 9/1987 | (EP) . |
| 5,394,882 | 3/1995 | Mawhinney . | | 0 872 643 A2 | 3/1988 | (EP) . |
| 5,398,673 | 3/1995 | Lambert . | | 298 367 A2 | 1/1989 | (EP) . |
| 5,404,871 | 4/1995 | Goodman et al. . | | 0388 525 A1 | 9/1990 | (EP) . |
| 5,413,111 | 5/1995 | Wilkinson . | | 0 425 092 A1 | 5/1991 | (EP) . |
| 5,433,193 | 7/1995 | Sanders et al. . | | 0 452 001 A2 | 10/1991 | (EP) . |
| 5,438,980 | 8/1995 | Phillips . | | 0 461 281 A1 | 12/1991 | (EP) . |
| 5,443,061 | 8/1995 | Champain et al. . | | 481 459 A1 | 4/1992 | (EP) . |
| 5,443,075 | 8/1995 | Holscher . | | 0549299 A2 | 6/1993 | (EP) . |
| 5,458,137 | 10/1995 | Axe et al. . | | 606 687 A2 | 7/1994 | (EP) . |
| 5,479,920 | 1/1996 | Piper et al. . | | 0705615 A1 | 9/1994 | (EP) . |
| 5,483,969 | 1/1996 | Testerman et al. . | | 0 714 670 A2 | 12/1994 | (EP) . |
| 5,490,502 | 2/1996 | Rapoport et al. . | | 0651971 A1 | 5/1995 | (EP) . |
| 5,492,113 | 2/1996 | Estes et al. . | | 0 656 216 A2 | 6/1995 | (EP) . |
| 5,503,146 | 4/1996 | Froehlich et al. . | | 0 661 071 A1 | 7/1995 | (EP) . |
| 5,507,282 | 4/1996 | Younes . | | 178 925 A2 | 4/1996 | (EP) . |
| 5,509,404 | 4/1996 | Lloyd et al. . | | 0 709 107 A1 | 5/1996 | (EP) . |
| 5,513,631 | 5/1996 | McWilliams . | | 0 714 670 A2 | 6/1996 | (EP) . |
| 5,517,983 | 5/1996 | Deighan et al. . | | 0 765 631 A2 | 4/1997 | (EP) . |
| 5,522,382 | 6/1996 | Sullivan et al. . | | 0 774 269 A1 | 5/1997 | (EP) . |
| 5,526,805 | 6/1996 | Lutz et al. . | | 0 788 805 A2 | 8/1997 | (EP) . |
| 5,535,738 | 7/1996 | Estes et al. . | | 2 596 279 | 3/1986 | (FR) . |
| 5,535,739 | 7/1996 | Rapoport et al. . | | 2 574 657 A1 | 6/1986 | (FR) . |
| 5,537,997 | 7/1996 | Mechlenburg et al. . | | 2 672 221 | 8/1992 | (FR) . |
| 5,540,219 | 7/1996 | Mechlenburg et al. . | | 2682042 A1 | 4/1993 | (FR) . |
| 5,540,220 | 7/1996 | Gropper et al. . | | 2 733 688 | 5/1995 | (FR) . |
| 5,540,222 | 7/1996 | Younes . | | 1432572 | 4/1976 | (GB) . |
| 5,540,733 | 7/1996 | Testerman et al. . | | 1 444 053 | 7/1976 | (GB) . |
| 5,546,933 | 8/1996 | Rapoport et al. . | | 1 583 273 | 1/1981 | (GB) . |
| 5,546,934 | 8/1996 | Kaigler et al. . | | 2 077 444 | 12/1981 | (GB) . |
| 5,546,952 | 8/1996 | Erickson . | | 2 097 272 | 11/1982 | (GB) . |
| 5,549,106 | 8/1996 | Gruenke et al. . | | 2 147 506 | 5/1985 | (GB) . |
| 5,549,555 | 8/1996 | Erickson . | | 2 164 569 | 3/1986 | (GB) . |
| 5,551,418 | 9/1996 | Estes et al. . | | 2 166 871 | 5/1986 | (GB) . |
| 5,551,419 | 9/1996 | Froehlich et al. . | | 2 205 167 | 11/1988 | (GB) . |
| 5,558,099 | 9/1996 | Bowman et al. . | | 2 221 302 | 1/1990 | (GB) . |
| 5,567,127 | 10/1996 | Wentz . | | 2 254 700 | 10/1992 | (GB) . |
| 5,588,439 | 12/1996 | Hollub . | | 2 261 290 | 5/1993 | (GB) . |
| 5,598,838 | 2/1997 | Servidio et al. . | | 2 271 811 | 4/1994 | (GB) . |
| 5,603,315 | 2/1997 | Sassor, Jr. . | | 2 294 400 | 5/1996 | (GB) . |
| 5,605,151 | 2/1997 | Lynn . | | 54-104369 | 8/1979 | (JP) . |
| 5,617,846 | 4/1997 | Graetz et al. . | | 60/212607 | 4/1984 | (JP) . |
| 5,632,269 | 5/1997 | Zdrojkowski . | | 62-103297 | 4/1987 | (JP) . |
| 5,645,053 | 7/1997 | Remmers et al. . | | 63-275352 | 11/1988 | (JP) . |
| 5,645,054 | 7/1997 | Cotner et al. . | | 2-173397 | 12/1988 | (JP) . |
| 5,647,351 | 7/1997 | Wesimann et al. . | | 4-70516 | 3/1992 | (JP) . |
| 5,655,522 | 8/1997 | Mechlenburg et al. . | | 06249741 | 9/1994 | (JP) . |
| 5,682,878 | 11/1997 | Ogden . | | 6-249742 | 9/1994 | (JP) . |
| 5,704,345 | 1/1998 | Berthon-Jones . | | 07280609 | 10/1995 | (JP) . |
| 5,715,812 | 2/1998 | Deighan et al. . | | 8019610 | 1/1996 | (JP) . |
| | | | | 467041 | 5/1992 | (SE) . |
| | FOREIGN PATENT DOCUMENTS | | | 1710064 A1 | 2/1994 | (SE) . |
| 79174/94 | 6/1995 | (AU) . | | WO 80/01044 | 5/1980 | (WO) . |
| 34471/95 | 2/1996 | (AU) . | | WO 82/03326 | 10/1982 | (WO) . |
| 40711/95 | 4/1996 | (AU) . | | WO 82/03548 | 10/1982 | (WO) . |
| 34354/95 | 5/1996 | (AU) . | | WO 86/05965 | 10/1986 | (WO) . |
| 3015279 A1 | 10/1881 | (DE) . | | WO 86/06969 | 12/1986 | (WO) . |
| 459104 | 4/1928 | (DE) . | | WO 87/02577 | 5/1987 | (WO) . |
| 3345067 A1 | 6/1984 | (DE) . | | WO 88/10108 | 12/1988 | (WO) . |
| 3429345 A1 | 6/1985 | (DE) . | | WO 89/05669 | 6/1989 | (WO) . |
| 34 02 603 A1 | 8/1985 | (DE) . | | WO 89/09565 | 10/1989 | (WO) . |
| 3537507 A1 | 4/1987 | (DE) . | | WO 90/14121 | 11/1990 | (WO) . |
| 3539073 A1 | 5/1987 | (DE) . | | WO 91/12051 | 8/1991 | (WO) . |
| 4432219 C1 | 4/1996 | (DE) . | | WO 92/11054 | 7/1992 | (WO) . |
| 29612119 U1 | 12/1996 | (DE) . | | WO 92/15353 | 9/1992 | (WO) . |
| 0 062 166 A2 | 10/1982 | (EP) . | | WO 92/22244 | 12/1992 | (WO) . |

| | | |
|---|---|---|
| WO 93/08857 | 5/1993 | (WO) . |
| WO 93/09834 | 5/1993 | (WO) . |
| WO 93/21982 | 11/1993 | (WO) . |
| WO 93/24169 | 12/1993 | (WO) . |
| WO 94/04071 | 3/1994 | (WO) . |
| WO 94/16759 | 8/1994 | (WO) . |
| WO 94/20018 | 9/1994 | (WO) . |
| WO 94/20051 | 9/1994 | (WO) . |
| WO 94/22517 | 10/1994 | (WO) . |
| WO 94/23780 | 10/1994 | (WO) . |
| WO 95/19814 * | 7/1995 | (WO) . |
| WO 95/32016 | 11/1995 | (WO) . |
| WO 96/32055 | 10/1996 | (WO) . |
| WO 96/36279 | 11/1996 | (WO) . |
| WO 96/39216 | 12/1996 | (WO) . |
| WO 96/40336 | 12/1996 | (WO) . |
| WO 96/40337 | 12/1996 | (WO) . |
| WO 96/40338 | 12/1996 | (WO) . |
| WO 96/41571 | 12/1996 | (WO) . |
| WO 97/02064 | 1/1997 | (WO) . |
| WO 97/05824 | 2/1997 | (WO) . |
| WO 97/06844 | 2/1997 | (WO) . |
| WO 97/09090 | 3/1997 | (WO) . |
| WO 97/10019 | 3/1997 | (WO) . |
| WO 97/10868 | 3/1997 | (WO) . |
| WO 97/15343 | 5/1997 | (WO) . |
| WO 97/18752 | 5/1997 | (WO) . |
| WO 97/20499 | 6/1997 | (WO) . |
| WO 97/22377 | 6/1997 | (WO) . |
| WO 97/28838 | 8/1997 | (WO) . |
| WO 97/41812 | 11/1997 | (WO) . |

OTHER PUBLICATIONS

Puritan Bennett; Clean, Quiet, and Comfortable . . . The Companion's 515 Nasal CPAP System; 6/88.

DeVilbiss Night Guard Nasal CPAP for the Treatment of Obstructive Sleep Apnea.

Sunrise; DeVilbiss Horizon LT 8001 Nasal CPAP Therapy Small in Size, big on features; 8/97.

Devilbiss; Revitalizer Soft Start; The Facts Speak for Themselves, 1992.

Tranquility; Performance CPAP Advantage.

Healthdyne International; Tranquility Plus.

Respironics Inc.; Respironics' Solo CPAP System Provides Simplified OSA Therapy at an Outstanding value; Sep. 19, 1996.

Respironics Inc.; The First Family of OSA Therapy; 1991.

Fisher & Paykel Healthcare; HC200 Series Nasal CPAP Blower & Heated Humidifier.

Pierre Medical; Morphee Plus appareil de traitement des apnees du sommeil manuel d'utilisation.

Weinmann:Hamburg: Somnotron nCPAP–Great WM 2300, 11/91.

Puritan Bennett; 515a Part of Our Blueprint for the Future; 03/90.

Puritan Bennett; Companion 320 I/E Bi–Level Respiratory System; 4/93.

ResMed; Sullivan VPAP II & II ST.

ResMed; The Sullivan V Family of CPAP Systems; 1996.

ResMed; The AutoSet Portable II; 1997.

ResMed; Sullivan Nasal CPAP System.

ResMed; The Sullivan IIID; 1995.

ResMed; The Sullivan Comfort; 1996.

DeVilbiss a Division of Sunrise Medical; Expand your Horizons With The Horizons; 1995.

Healthdyne Technologies; Home Health Care Dealer; The Journal of Home Medical Equipment and Services/Supplier; Nov. and Dec. 1997.

Healthdyne International; Tranquility Quest, The Compact CPAP for Greater patient comfort.

AirStep; Medical Products . . . Stand the Test of Time.

MAP Medical Progress for Physician und Patient; The Gentle Therapy for Sleep–Related Breathing Disorders.

Taema; Ventilation CP 90.

DPAP; Breath, by breath, by breath.

Lifecare; Smallest. Quietest. Smartest.

Lifecare; Quiet CPAP System for Maximum Compliance; 1991.

Lifecare; Software Nasal Mask, Custom Nasal Masks; 1991.

Nidek Medical; Silenzio.

Weinmann; Just to Fell Well, Sensitive Sleep Apnea Therapy with Somnotron 3 and Somno–Mask System.

Respironics Inc.; Aira CPAP System; 1993.

Respironics Inc.; SleepEasy III A New Dawn in Patient Compliance.

Respironics Inc.; Muliple Choice REMstar Choice Nasal CPAP System.

MaxII nCPAP and Moritz II Bi–Level Brochure.

* cited by examiner

CONTROL OF DELIVERY PRESSURE IN CPAP TREATMENT OR ASSISTED RESPIRATION

FIELD OF THE INVENTION

The present invention relates to apparatus for the control of delivery pressure of air or breathable gas in continuous positive airway pressure (CPAP) treatment or assisted respiration. The CPAP treatment may be by way of delivery of a single therapeutic pressure of in a bi-level manner or an automatically adjusting CPAP manner.

BACKGROUND OF THE INVENTION

CPAP is a well known treatment for the temporary relief of conditions including obstructive sleep apnea (OSA) and snoring. By this technique, air (or other breathable gas) at a pressure elevated above atmospheric pressure is constantly supplied to the entrance to a patient's airway (by the nasal and/or oral route) by means of known arrangements of masks or nasal prongs. The elevated air pressure acts as a pneumatic splint of the patient's airway in the vicinity of the oro- and hypo-pharynx, reducing or eliminating the occurrences of apneas or hypopneas during sleep. A bi-level CPAP device delivers two distinct pressures during the patient's respiratory cycle; a relatively lower pressure during exhalation and a relatively higher pressure during inhalation. An automatically adjusting CPAP device may operate to provide a relatively low background pressure which increases to a therapeutic pressure on a needs basis, and preferably at a time to prevent the onset of an apnea.

Assisted respiration similarly provides a supply of air (or other breathable gas) at a pressure elevated above atmospheric pressure, although is concerned more with providing a sufficient flow of air (or other breathable gas), rather than regulating the pressure of air to a continuous (constant) level in the case of CPAP treatment.

In recent times, CPAP apparatus have been constituted by a nose and/or mouth mask coupled by a flexible air (or other breathable gas) delivery tube to a controllable flow generator. The flow generator includes a speed-controlled brushless DC motor connected with a fixed vane turbine. Control of the CPAP treatment pressure delivered to a patient's airway is conducted at the flow generator by speed control of the motor in response to signals issued by a microprocessor.

Whilst this arrangement provides satisfactory treatment of conditions such as OSA and snoring, it is desirable for alternative arrangements to be devised that can remove the pressure controls from the remote flow generator to being at or near the patient mask. This may lead to a reduction of the cost of CPAP treatment apparatus by removing the need for a power supply, microprocessor controller, motor and turbine. A practical concern in such an arrangement is that the mask not be made too heavy so as to disturb the patient in wearing the mask during sleep. Prior art delivery pressure controls located at a mask, such as breathing apparatus worn by military pilots, are heavy and cumbersome and not suitable to being worn during sleep when a patient's neck and shoulder muscles necessarily need to be in a relaxed state.

It is an object of the present invention to provide delivery pressure control apparatus that can be incorporated at or near a patient mask and that is not uncomfortable or cumbersome to the patient when worn during sleep.

SUMMARY OF THE INVENTION

Accordingly, in a first aspect, the present invention discloses a pressure control apparatus for CPAP treatment or assisted respiration, said apparatus comprising:

an inlet chamber for connection to a primary supply of air or other breathable gas at a pressure at or above a maximum treatment pressure;

an outlet chamber for communication with a mask or the like;

a diaphragm for communication with a portion of said outlet chamber;

means to provide a predetermined force to said diaphragm;

a first valve means operable to open a flow path between said outlet chamber and said inlet chamber in response to deflection of said diaphragm in a first direction; and a second valve means operable to provide an exhaust path from said outlet chamber to atmosphere in response to deflection of said diaphragm in a second direction opposite first direction; and wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open.

In a second aspect, the present invention discloses a method of administering CPAP treatment using the pressure control apparatus of the first aspect.

In a third aspect, the present invention discloses a method of administering assisted respiration using the pressure control apparatus of the first aspect.

In a fourth aspect, the present invention discloses a delivery pressure control apparatus for CPAP treatment or assisted respiration, said apparatus comprising:

an input chamber for connection to a supply of air at a pressure at or above maximum treatment pressure;

a pressure reducing means or flow restricting means for communication with said supply of air to provide air at a reduced pressure corresponding to a treatment pressure to a sensing chamber;

an outlet chamber for communication with a mask or the like;

a diaphragm arranged between a portion of the outlet chamber and a portion of the sensing chamber;

first valve means located between said outlet chamber and said inlet chamber and operable to open a flow path between said outlet chamber and said inlet chamber upon deflection of said diaphragm; and a second valve means located between said outlet chamber and atmosphere, and operable to provide an exhaust path to atmosphere from said outlet chamber on opposed deflection of said diaphragm; and wherein when the pressure of air in said outlet chamber reduces below the pressure of air in said sensing chamber said diaphragm deflects to operate said first valve means to cause an equilibrating flow of air from said inlet chamber, and further wherein when the pressure of air in said outlet chamber exceeds that of said sensing chamber, said diaphragm deflects to open said exhaust path from said outlet chamber.

In an advantageous form, the pressure reducing means or flow restricting means is controllable to select a desired therapeutic or treatment pressure.

Advantageously, the first and second valve means can comprise a valve body that can block an opening constituting said flow path and an opening constituting said exhaust path respectively, and an elongate tail extending away from the valve body to the distal end of the tail being engaged by said diaphragm.

In a fifth aspect, the present invention disclose CPAP treatment apparatus comprising:
(a) a supply of air at a pressure at or above maximum treatment pressure;
(b) a mask for continuous delivery of air at a treatment pressure elevated above atmospheric pressure; and
(c) delivery pressure control apparatus integral of, or proximate to said mask, said apparatus including:
an input chamber for connection to said supply of air;
a pressure reducing means or flow restricting means for communication with said supply of air to provide air at a reduced pressure corresponding to a treatment pressure to a sensing chamber;
an outlet chamber for communication with said mask;
a diaphragm arranged between a portion of the outlet chamber and a portion of the sensing chamber;
first valve means located between said outlet chamber and said inlet chamber and operable to open a flow path between said outlet chamber and said inlet chamber upon deflection of said diaphragm; and
a second valve means located between said outlet chamber and atmosphere, and operable to provide an exhaust path to atmosphere from said outlet chamber on opposed deflection of said diaphragm; and
wherein when the pressure of air in said outlet chamber reduces below the pressure of air in said sensing chamber upon inhalation said diaphragm deflects to operate said first valve means to cause an equilibrating flow of air from said inlet chamber, and further wherein when the pressure of air in said outlet chamber exceeds that of said sensing chamber upon exhalation said diaphragm deflects to open said exhaust path from said outlet chamber.

The supply of air can, for example, be a constant speed blower, positive displacement pump or bottled gas, connected to said delivery pressure control apparatus by a tube.

While the delivery pressure control apparatus can be located at or proximate the mask, it alternatively can be located remote from the mask, connected thereto by a tube and preferably by a flexible tube.

Embodiments of the invention can provide non-complex CPAP treatment apparatus that does not rely upon any electronic components, and thus is relatively less expensive that conventional CPAP apparatus.

DESCRIPTION OF THE DRAWINGS

Embodiments of the invention now will be described with reference to the accompanying drawings, in which.

DESCRIPTION OF THE PREFERRED EMBODIMENTS

Through the pressure reducing means or flow restricting means controlling the pressure to the sensing chamber, it is possible to vary the pressure within the mask.

Through the pressure reducing means or flow restricting means varying the pressure to the sensing chamber to achieve a predetermined mask pressure for inhalation and another predetermined mask pressure for exhalation, the invention may operate in a bi-level manner.

Through the pressure reducing means or flow restricting means varying over time the pressure to the sensing chamber in a manner that corresponds with the determined pressure needs of the patient, the invention may operate in an automatically adjusting CPAP system. By any suitable means the patient is monitored and the patient's pressure needs determined and by suitable adjustment the pressure reducing means or flow restricting means varies the pressure in the sensing chamber, thereby resulting in the required mask pressure.

Furthermore, by slowly adjusting the pressure reducing means or flow restricting means and thereby slowly increasing the pressure to the sensing chamber over a succession of breaths it is possible to increase the pressure applied to the patient. In this manner the invention operates to ramp up the pressure delivered to the patient. Such ramping is particularly useful at the time of first fitting the mask.

Figure 1:
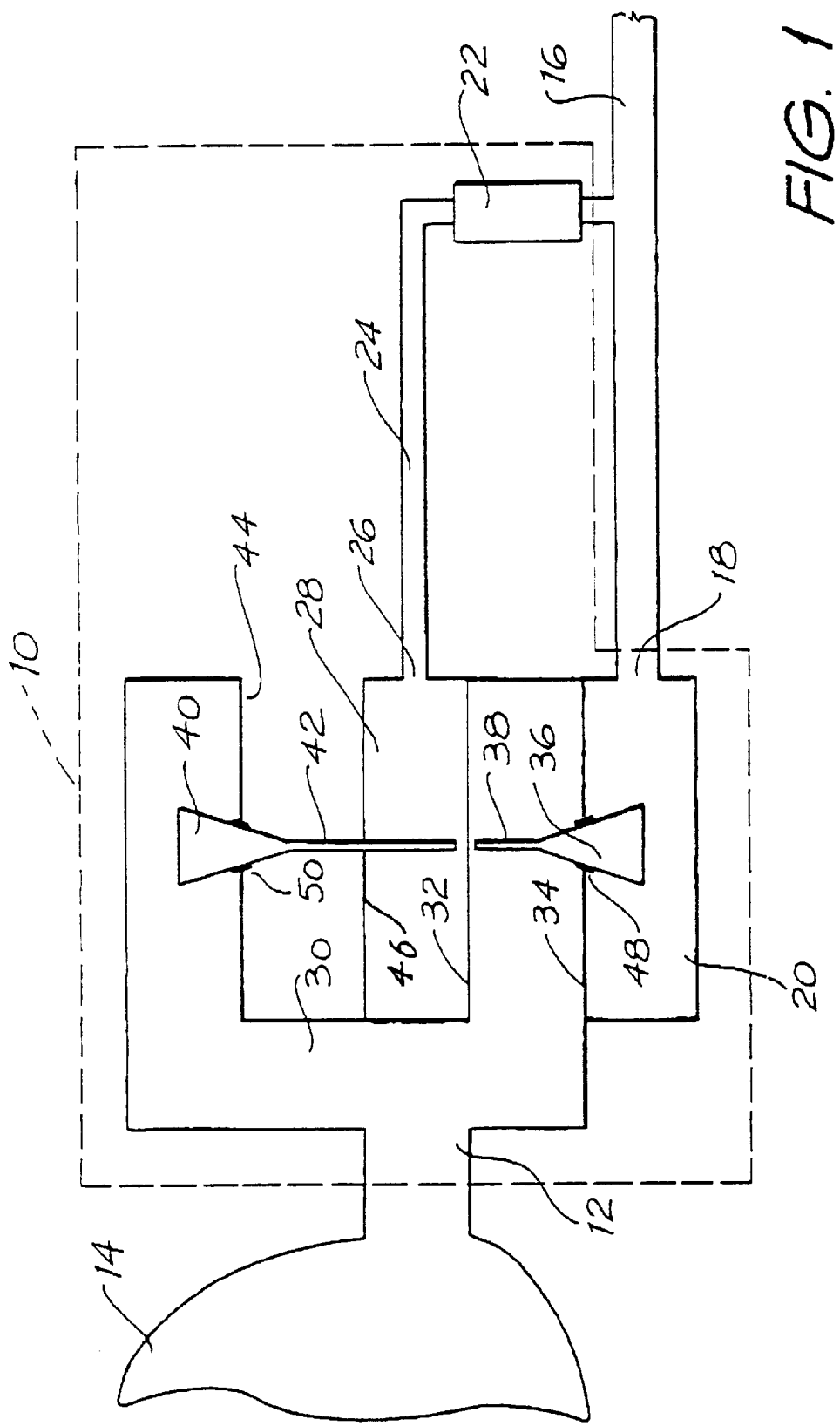
FIG. 1 is a schematic view of a first embodiment of a delivery pressure controlling apparatus.
Figure 2:
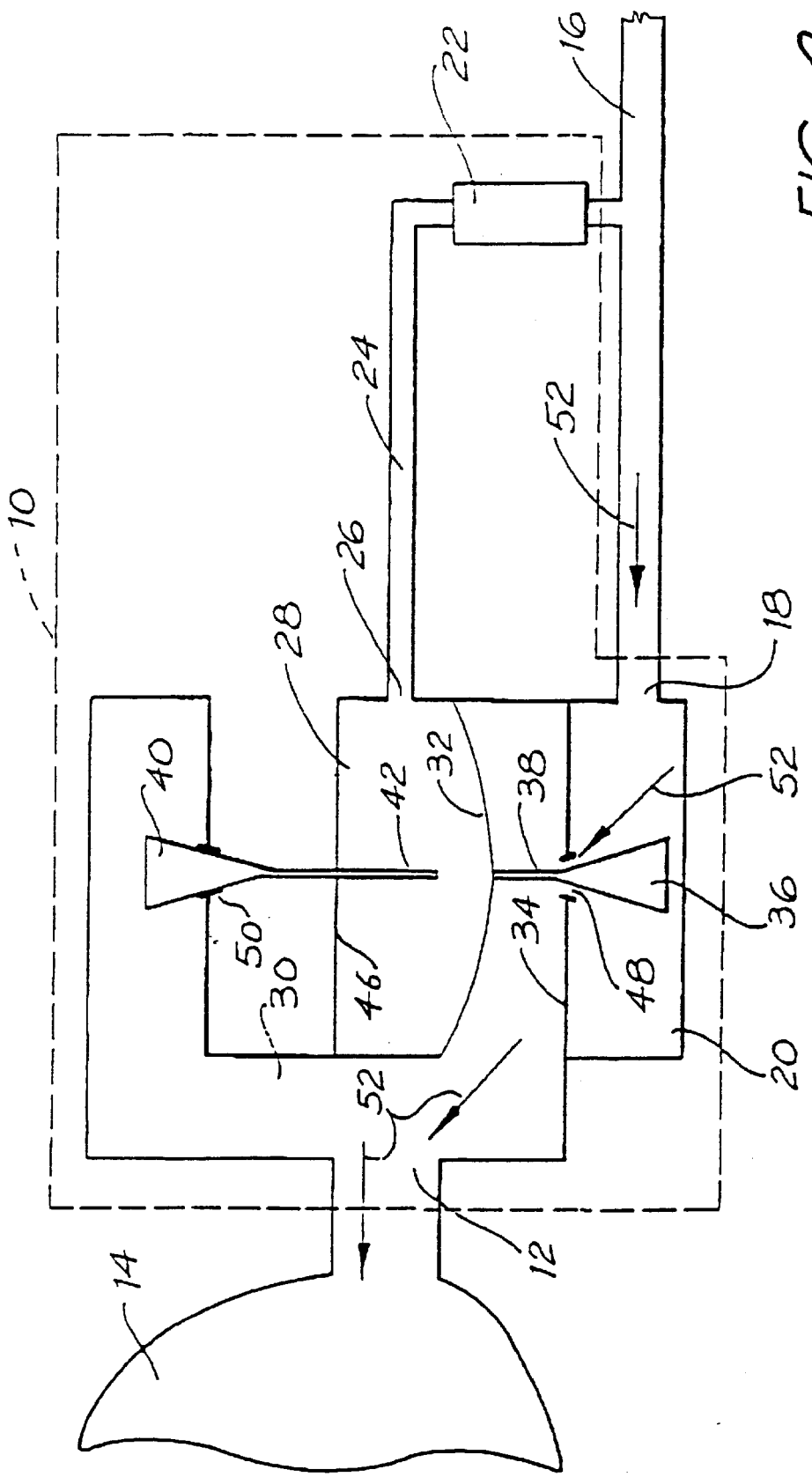
FIG. 2 is the embodiment of FIG. 1 during inhalation.
Figure 3:
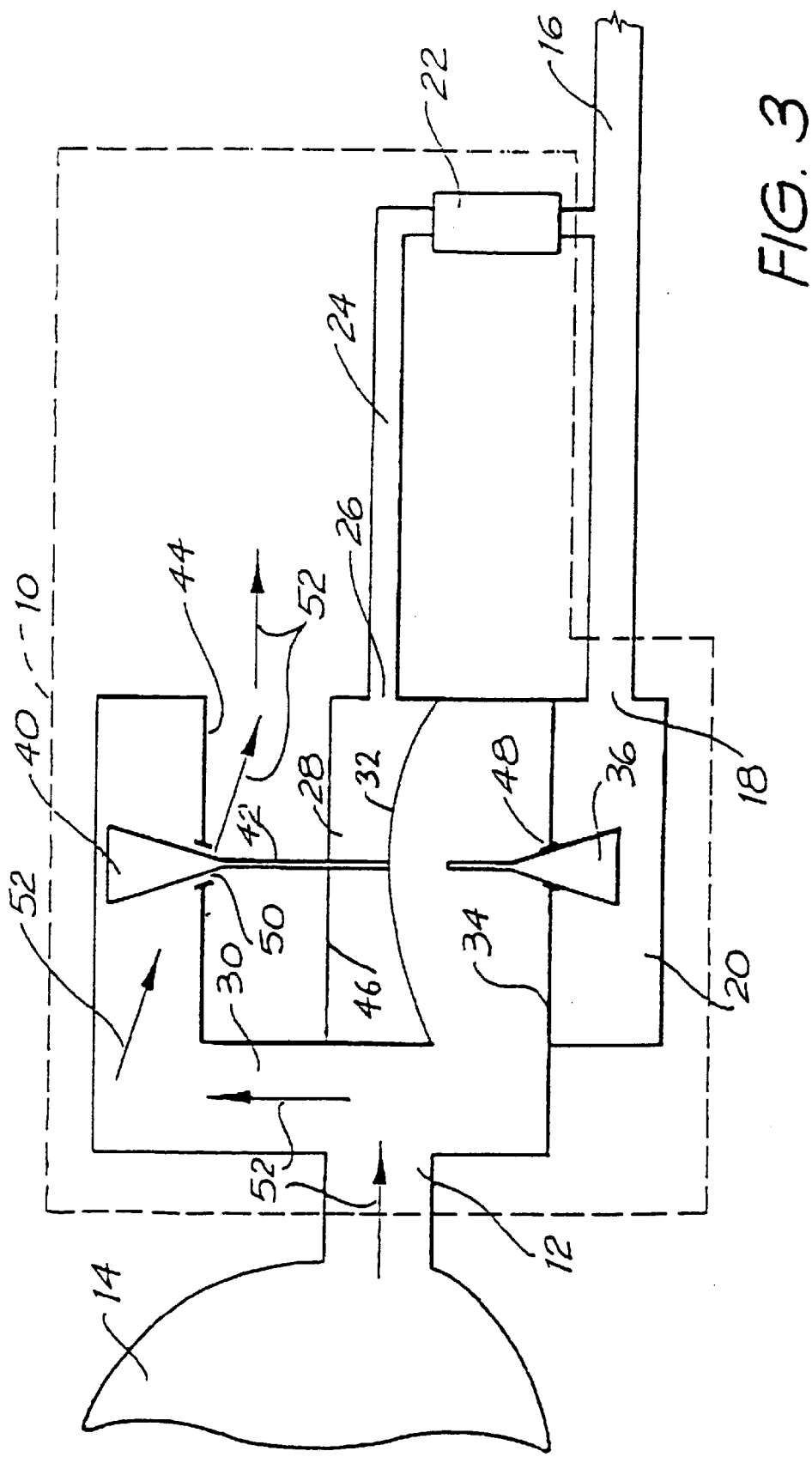
FIG. 3 is the embodiment of FIG. 1 during exhalation.

Referring firstly to FIGS. 1 to 3 a first embodiment of a delivery pressure controlling apparatus 10 is shown. An outlet 12 of the apparatus 10 is connected to a mask 14 suitable to be worn by a patient to cover their nose and/or mouth, whereby air at a pressure elevated above atmospheric pressure can be supplied to the entrance to the patient's airway, via the mask 14, by the nasal and/or oral route. The controlling apparatus 10 can be carried on the same frame or shell (not shown) as the cushion of the mask 14. The pressure controlling apparatus 10 has further connection with a delivery tube 16 by which a supply of pressurized air (the "primary" air supply) is provided through an inlet 18 to an inlet chamber 20 of the pressure controlling apparatus 10. The pressure of air in the delivery tube 16, and hence in the inlet chamber 20, is at or above the maximum patient treatment pressure, as presently will be explained.

The primary supply of pressurized air to the delivery tube 16 can be by any convenient means (not shown), including a fixed speed induction machine capable of operating from a mains voltage, thus not requiring a regulated or switched mode power supply as is common with the prior art, or alternatively by a positive displacement bellows arrangement or a gas supply bottle. The pressure of air in the delivery tube can be in the range of about 50–100 cm $H_2O$, meaning that the delivery tube 16 can be in the range about 10–12 mm diameter, which is a reduction of 50% in diameter over prior art arrangements. The reduced diameter results in greater comfort for the patient, and because the pressure is well above treatment pressure, flow induced losses can be tolerated and a long length of tubing utilised to the extent that the supply of air can be located in a different room to the patient to reduce noise and thereby increase patient comfort.

A pressure reducing valve 22 also has connection with the delivery tube 16 to supply air at a reduced pressure (the "secondary" air supply) via a conduit 24 passing through an inlet 26 to a sensing chamber 28. The pressure reducing valve 22 is controllable to select a desired and predetermined patient treatment pressure, meaning that the pressure of air within the sensing chamber 28 is at the predetermined patient treatment pressure.

The sensing chamber 28, in part, is physically separated from an outlet chamber 30 by an elastic diaphragm 32.

The wall 34 between the inlet chamber 20 and the exhaust chamber 30 includes an opening 48 be opened or closed under the influence of a tapered plug valve member 36 to provide a flow path of air from the inlet chamber 20 to the outlet chamber 30. The plug valve member 36 has a tail 38 that ends proximate the diaphragm 32.

A further tapered plug valve member 40, also having a tail 42, extends through a wall 44 of the exhaust chamber 30 and through a wall 46 of the sensing chamber 28. The wall 44 includes an exhaust opening or port 50 sealable by the valve member 40, that when opened provides an exhaust path from the exhaust chamber 30 to atmosphere.

FIGS. 2 and 3 show the operation of the apparatus 10 during patient inhalation and exhalation respectively. The direction of air flow is represented by arrows 52.

As shown in FIG. 2, on inhalation by the patient, the pressure of air within the outlet chamber 30 reduces instantaneously with flow, resulting in the pressure in the sensing chamber 28 being greater than in the outlet chamber 30. This force or pressure differential causes the diaphragm 32 to deflect downwards to engage the tail 38 and cause the opening 48 to allow a path of inlet air from the inlet chamber 20 to pass to the outlet chamber 30 and so to the patient.

As shown in FIG. 3, on patient exhalation (expiration), the pressure within the outlet chamber 30 increases to a level higher than the treatment pressure in the sensing chamber 28. The force or pressure differential results in the diaphragm 32 deflecting upwardly to engage the tail 42 and lift the valve member 40 clear of the opening 50 thus allowing an exhaust path of air to atmosphere.

Following the individual events of inspiration and expiration, the pressure within the outlet chamber 30 equilibrates returning the diaphragm 32 to the neutral position (as shown in FIG. 1), closing both of the chamber openings 48,50 by reseating of the respective valve members 36,40.

Deflection of the diaphragm 32 occurs during each inspiratory and expiratory event, meaning the respective valve members 36,40 are operated once per respiratory cycle respectively. The sensitivity of the diaphragm 32 will be such as to operate for a pressure differential of ±1 cm $H_2O$, so that the treatment pressure will be regulated to within ±1 cm $H_2O$.

Figure 4:
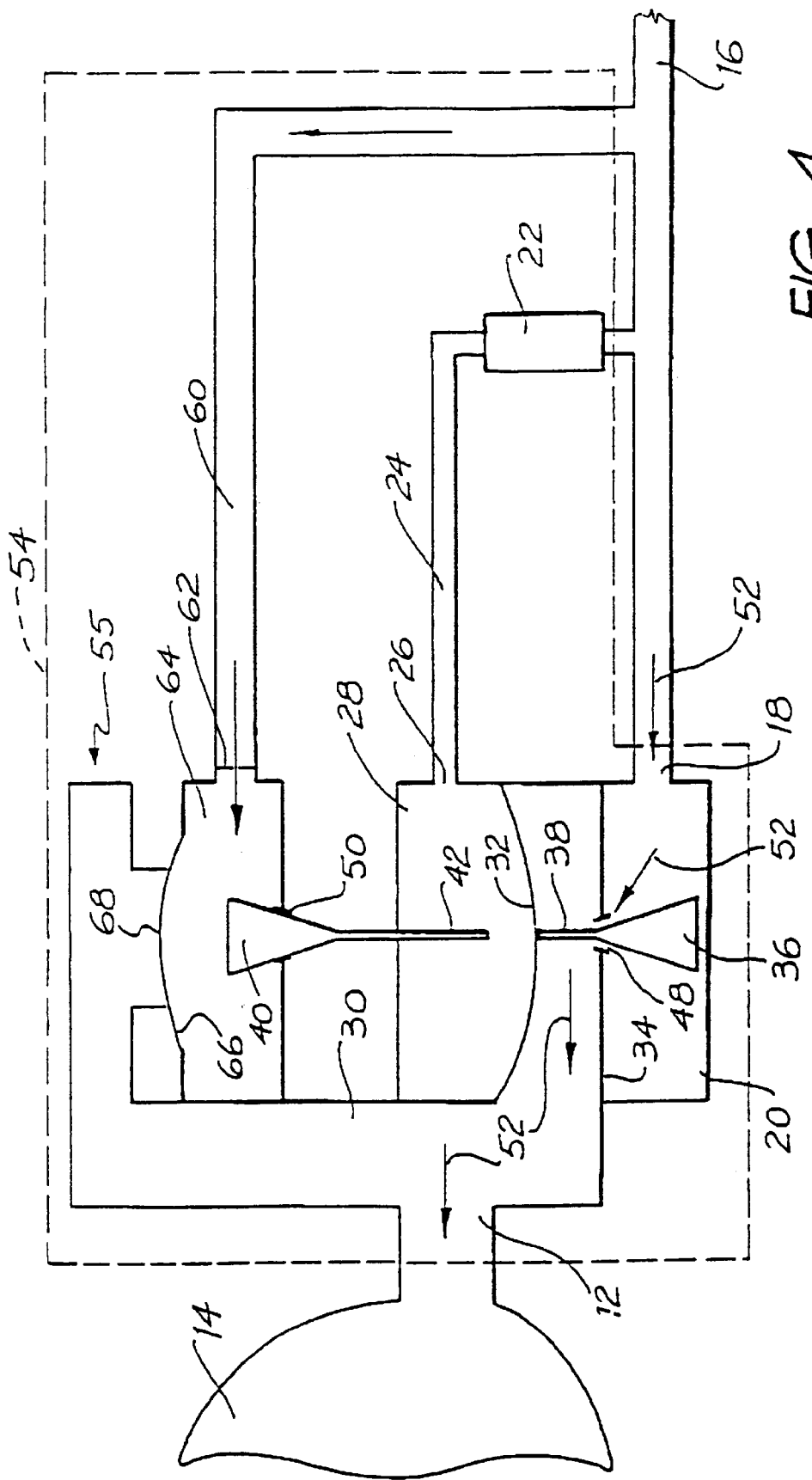
FIG. 4 is a schematic view of a second embodiment of a delivery pressure controlling apparatus during inhalation.
Figure 5:
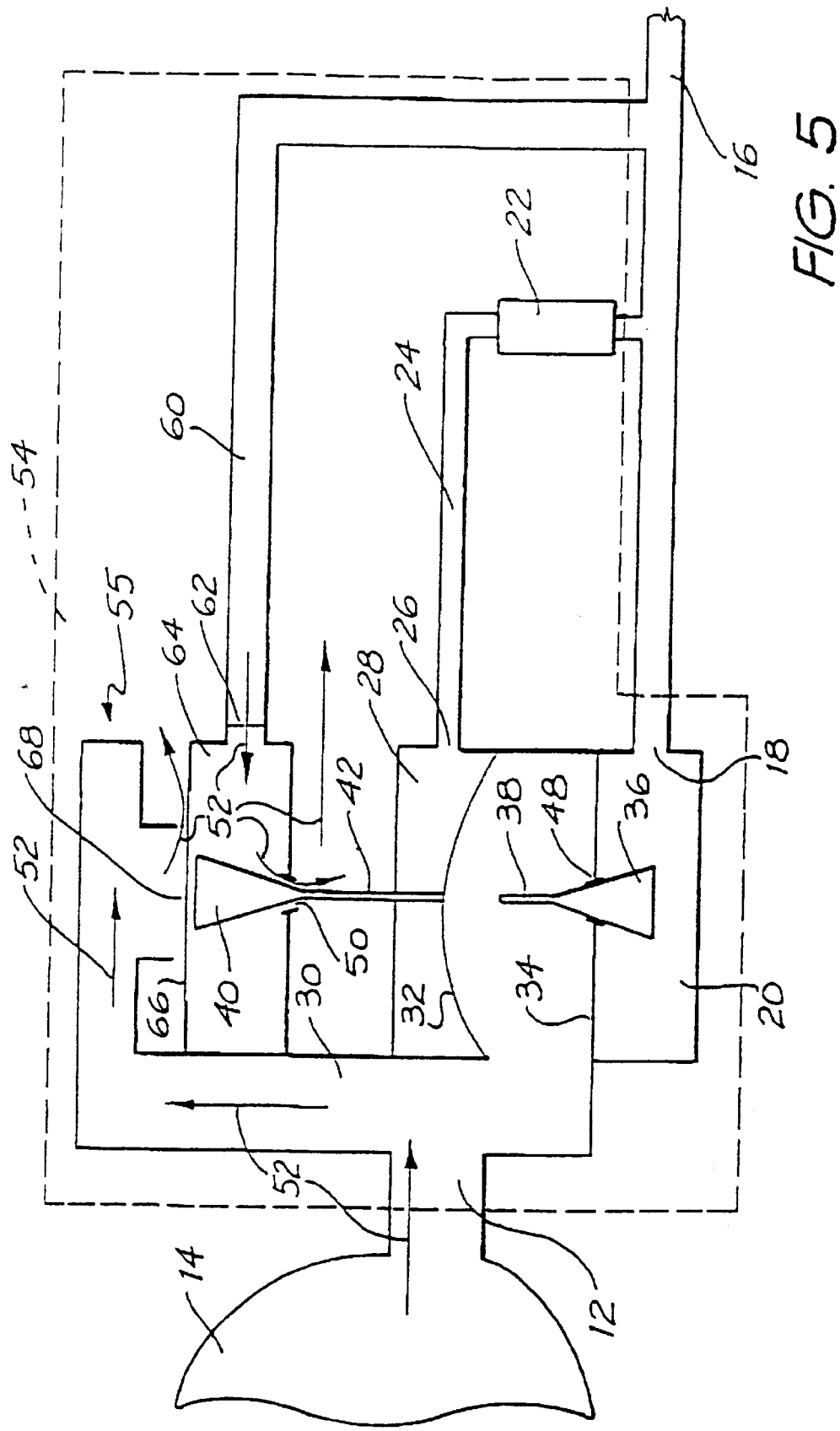
FIG. 5 is the embodiment of FIG. 4 during exhalation.

FIGS. 4 and 5 show a second embodiment of a delivery pressure controlling apparatus 54 that utilises a form of exhaust servo-valve 55. Like reference numerals to those used in describing the first embodiment are used to indicate like features. During inhalation, the delivery pressure controlling apparatus 54 operates in the same manner as described with reference to FIG. 2, except that the exhaust path is differently arranged and is not directly controlled by the exhaust valve member 40 as was the case in the first embodiment.

In the second embodiment, a high pressure branch line 60 from delivery tube 16 provides a supply of air via a flow restrictor 62 (the "tertiary" air supply) to a pilot or exhaust control chamber 64. The flow restrictor 62 provides a tertiary air supply between the pressures of the primary air supply and the secondary air supply (patient treatment pressure). The chamber 64 includes an exhaust port control diaphragm 66 that deflects under the greater pressure of air within the chamber 64 than in the outlet chamber 30 to close an exhaust port or opening therefrom.

Air flow on inhalation, as best shown in FIG. 4, thus is from the delivery tube 16 via the inlet chamber 20, through the opening 48 into the outlet chamber 30 and so to the patient via the mask 14, not being able to pass by the blocked exhaust opening 68.

During exhalation, as best shown in FIG. 5, the pressure of air within the outlet chamber 30 increases over that in the sensing chamber 28, causing upward deflection of the diaphragm 32, and upward displacement of the valve member 40 to open the exhaust opening 50, thereby shunting (or venting or bleeding) the pressurized air within the chamber 64 and allowing recovery of the diaphragm 66 to a near relaxed state, whereby the exhaust opening 68 is open to allow expired air to pass to atmosphere.

In both the first and second embodiments, the pressure reducing valve 22 can also be provided with a timer function that can be utilised to ramp the treatment pressure up to the required value over a selectable period of time, typically between 10 minutes to 1 hour upon commencement of CPAP treatment or respiratory assist.

Figure 6:
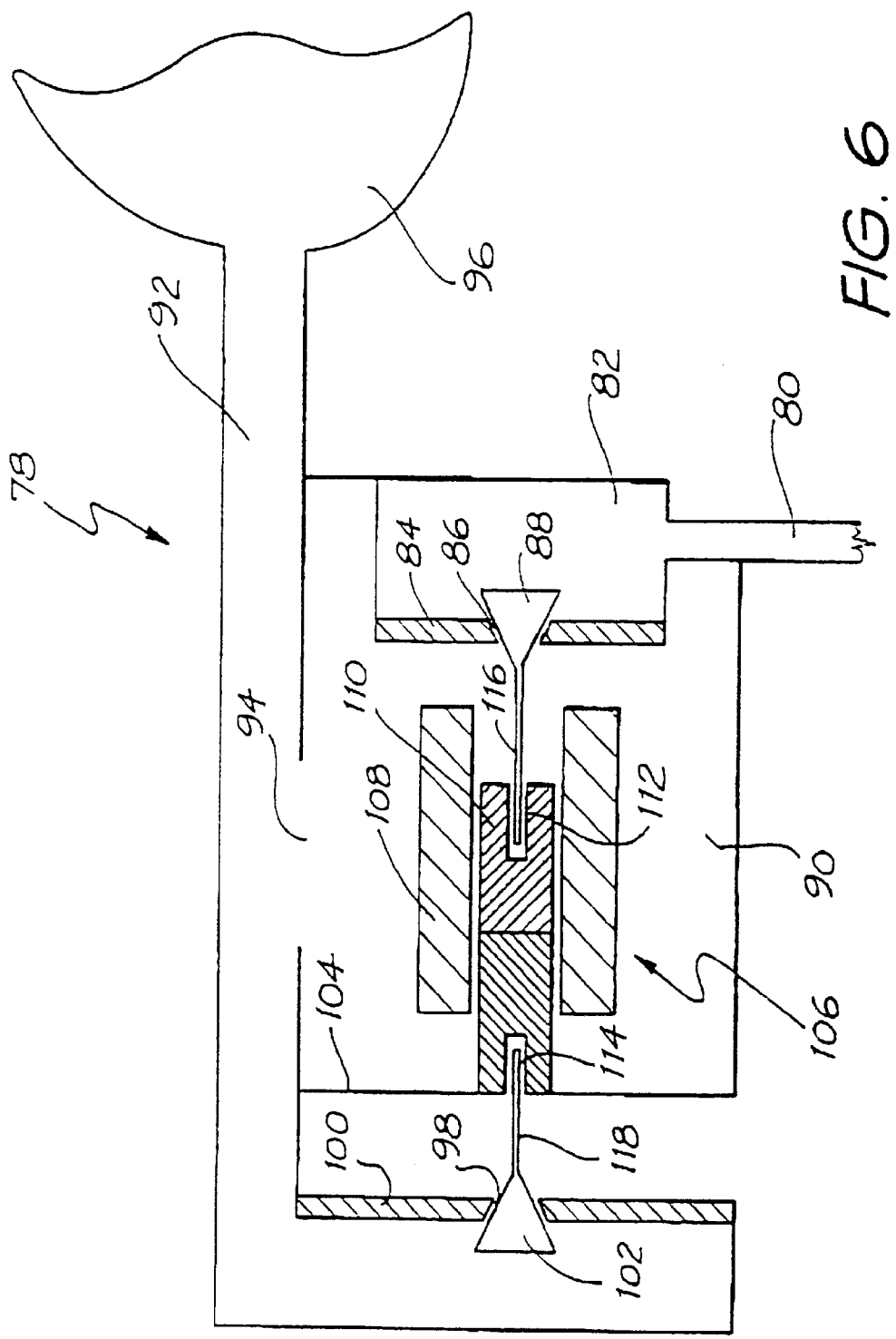
FIG. 6 is a schematic view of a third embodiment of a delivery pressure controlling apparatus.

FIG. 6 shows a third embodiment of a delivery pressure controlling apparatus 78 directed to the provision of bi-level CPAP treatment, by which a first treatment pressure is provided during patient inspiration and switched to a second and lower treatment pressure during the expiration phase of each respiratory cycle. In this embodiment, high pressure air above maximum treatment pressure is provided by a delivery tube 80 to an inlet chamber 82. The high pressure air can be provided by means such as those described with reference to the first and second embodiments. A wall 84 of the inlet chamber 82 has an opening 86 controllably opened or closed by a valve member 88. The opening 86 provides communication with an outlet chamber 90 that, in turn, has communication with a passage 92 by a aperture 94. The passage 92 is in turn in communication with a patient mask 96.

The passage 92 has a further exhaust opening 98 in a wall 100 thereof, the exhaust opening 98 being controllably opened or closed by an exhaust valve member 102.

Control of the inlet valve member 88 and the exhaust valve member 102 is by a combination of an elastic diaphragm 104 and an electromagnetic actuator 106. A coil assembly 108 surrounds a permanent magnet 110 which includes slots 112,114 at respective ends thereof within which are received extended actuating pins 116,188 of the inlet valve member 88 and the exhaust valve member 102 respectively. The diaphragm 104 is attached to the magnet 110 of the actuator. During inhalation, a predetermined DC current level is supplied to the coil 108 induce a predetermined force and cause the magnet 110 to move laterally to the right to engage the actuating pin 116 and cause the inlet valve member 88 to be displaced to a controlled degree and allow a predetermined pressure of air to build up within the outlet chamber 90 by passage of air through the controlled restriction of the opening 86.

The diaphragm 104 will be deflected toward the left by the increase of pressure within outlet chamber 90. Eventually the pressure within chamber 90 will increase to a point where the force produced by the deflection of the diaphragm in the left direction balances the predetermined force applied to the magnet 110 in the right direction by the coil 108. This causes the magnet 110 to return to its neutral position and cease to be in contact with the tail 116 of the valve 88. The valve 88 will then close.

During inspiration, the pressure within the outlet chamber 90 will drop; the force applied to the diaphragm 104 in the left direction will be lower than the predetermined force applied to the magnet 110 in the right direction. The magnet 110 will therefore be displaced by this force differential in the right direction to engage the actuating pin 116 of the valve 88. The valve 88 will reopen, air will flow from the inlet chamber 82 into outlet chamber 90 through the opening 86, forcing the diaphragm 104 in the left direction until the pressure force on the diaphragm 104 balances the predetermined electromagnetic force applied to the magnet 110 in the right direction by the coil 108.

During expiration, the pressure within the outlet chamber 90 will increase due to the connection of the outlet chamber 90 with the mask 96 by the opening 94. The pressure force applied to the diaphragm 104 will be greater than the force applied to the magnet 110 by the electromagnetic actuator 108. The diaphragm 104 will therefore be deflected to the left by this force differential and the magnet 110 will be in contact with the actuating pin 118 of valve 102. The valve 102 then opens and lets air from within the outlet chamber 90 escape to atmosphere through the opening 98. The valve 102 will remain open as long as the pressure force on diaphragm 104 is greater than the force applied to the magnet 110 by the electromagnetic actuator 108.

By controlling the current flowing into the electromagnetic actuator 108, it is possible to control the force applied to the magnet 110 and by increasing or decreasing this current it is possible to control the pressure within the mask.

By monitoring the patient breathing through a suitable system it is possible to switch the current flowing into the magnetic actuator 108 between selected levels or values in synchronism with the patient breathing. Switching of the pressure applied to the patient between 2 or more selected values, means a bi-level pressure range may be delivered.

It will be appreciated that by varying the current level to the electromagnetic actuator 108 it is possible to vary the pressure within the mask. By varying over time the current to the electromagnetic actuator in a manner that corresponds with the determined pressure needs of the patient the invention may operate in an automatically adjusting CPAP system. By any suitable means the patient is monitored and the patient's pressure needs determined and by suitable circuitry a suitable current is delivered to the electromagnetic actuator resulting in the required mask pressure.

Furthermore, by slowly increasing the current flowing into the magnetic actuator 108 over a succession of breaths it is possible to increase the pressure applied to the patient. In this manner the invention operates to ramp up the pressure delivered to the patient. Such ramping is particularly useful at the time of first fitting the mask.

FIGS. 7 to 12 show a fourth embodiment of a delivery pressure controlling apparatus 120 that also utilises a form of exhaust servo valve 180 similar to that described with respect to the second embodiment.

Figure 7:
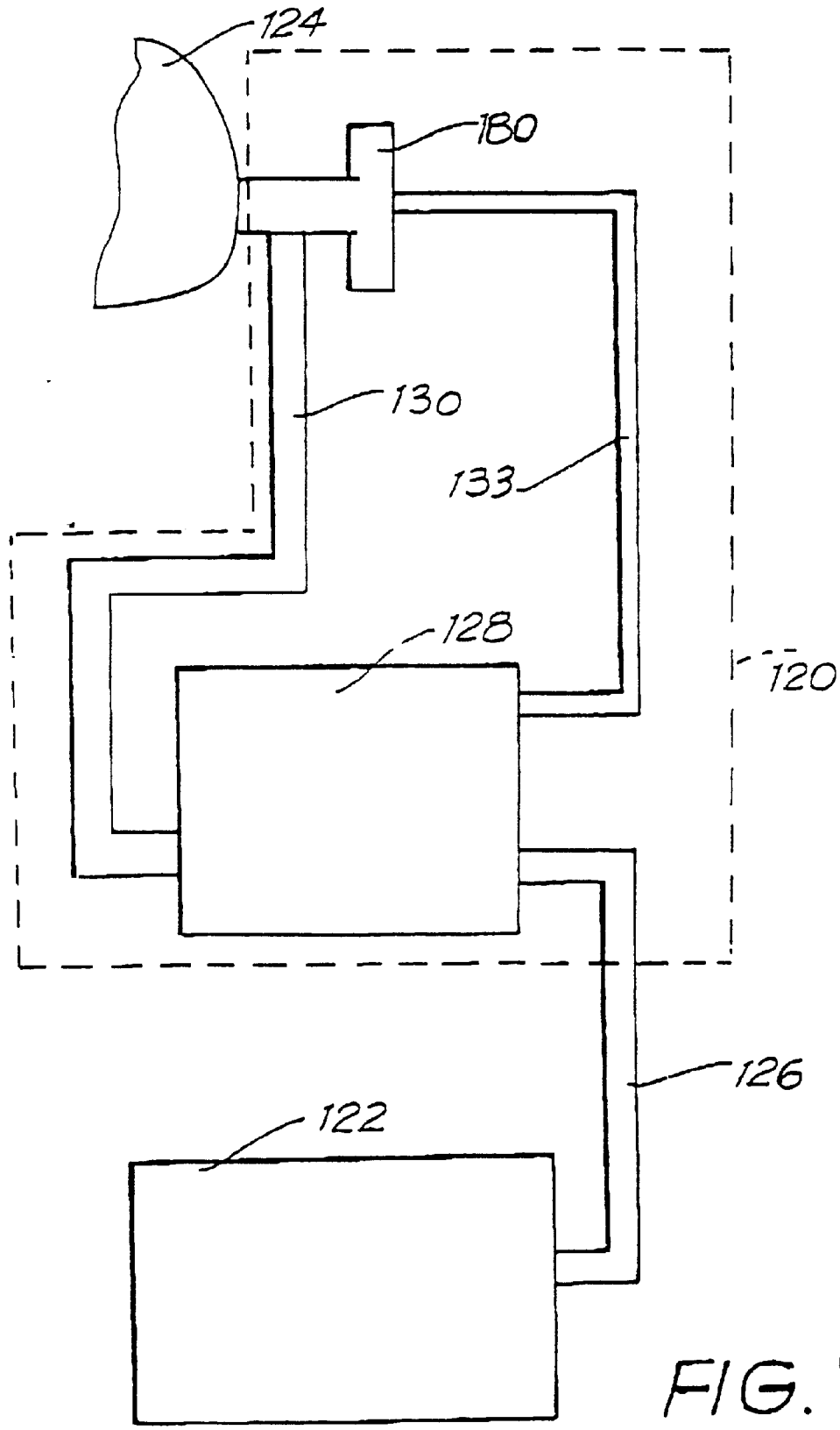
FIG. 7 is a schematic view of a fourth embodiment of a delivery pressure controlling apparatus incorporated into a CPAP system.

FIG. 7 shows a general arrangement of the apparatus 120 interposed between a primary supply of pressurized air 122 and a mask 124. The primary supply of pressurized air can be provided by means such as those described with reference to earlier embodiments.

The pressurized air supply 122 is connected to the apparatus 120 by a delivery tube 126. The delivery tube 126 is connected to the main body 128 of the apparatus 120. The main body 128 is connected to the mask 124 by mask supply tube 130 and to the exhaust servo valve 180 by an exhaust servo valve supply tube 133.

Figure 8:
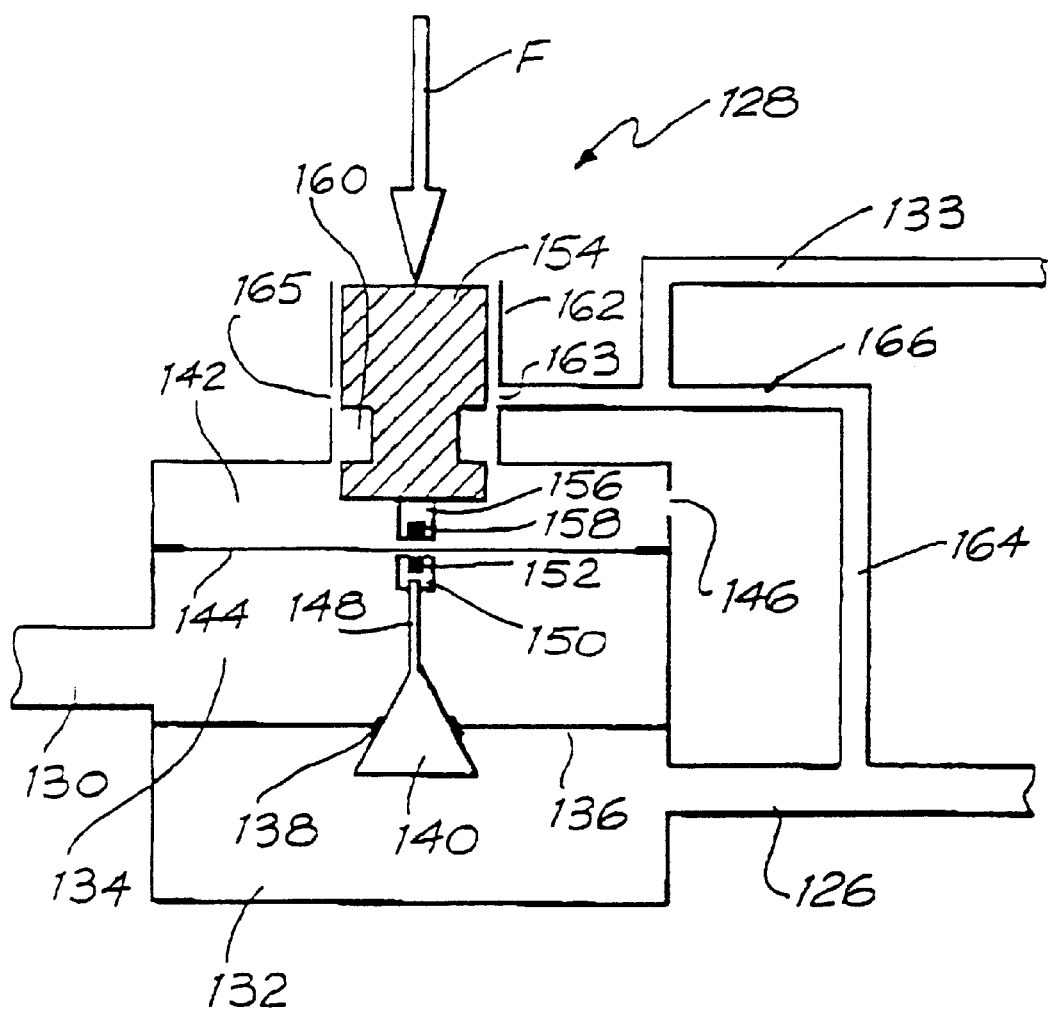
FIG. 8 is the main body of the embodiment of FIG. 7.

FIG. 8 is a schematic view of the main body 128. The main body 128 comprises an inlet chamber 132 which receives the pressurized primary air supply from the delivery tube 126. The inlet chamber 132 is physically separated from an outlet chamber 134 by a wall 136. The wall 136 includes an opening 138 which can be open or closed under the influence of a plug valve member 140. The outlet chamber 134 supplies air to the mask 124 via the tube 130 and is separated from a venting chamber 142 by an elastic diaphragm 144. The venting chamber 142 is open to atmosphere at opening 146. The valve member 140 includes a tail 148 terminating in a magnet holder 150 in which is located a magnet 152. On the other side of the membrane 144 there is located a control valve member 154 which also has a magnet holder 156 with a magnet 158 therein. The magnets 152 and 158 are configured or oriented to attract each other.

The control valve member 154 includes a circumferential groove 160 and is slidably retained within a valve member housing 162. The valve member 162 is adapted to provide a predetermined force to urge the control valve member 154 in the direction of arrow F towards the diaphragm 144 by virtue of it's own weight, or by having additional weights applied to it or by a spring bias arrangement or the like.

The delivery tube 126 also delivers air to an inlet 163 of the valve member housing 162 at a reduced pressure (the "secondary" air supply) through a branch delivery tube 164 having a flow restrictor 166 therein. The flow restrictor 166 can be constant or adjustable. The exhaust supply tube 133 is connected to the branch delivery tube 164 between the valve member housing and the flow restrictor 166 and, therefore, also supplies air at reduced pressure (the "tertiary" air supply) to the exhaust servo valve 132.

The housing 162 includes an outlet 165 to atmosphere. When the groove 160 of the valve member 154 is aligned with the opening 165 the air in the branch delivery tube 164 passes through the inlet 163 to the groove 160 and thereafter to atmosphere through the outlet 165.

Figure 11:
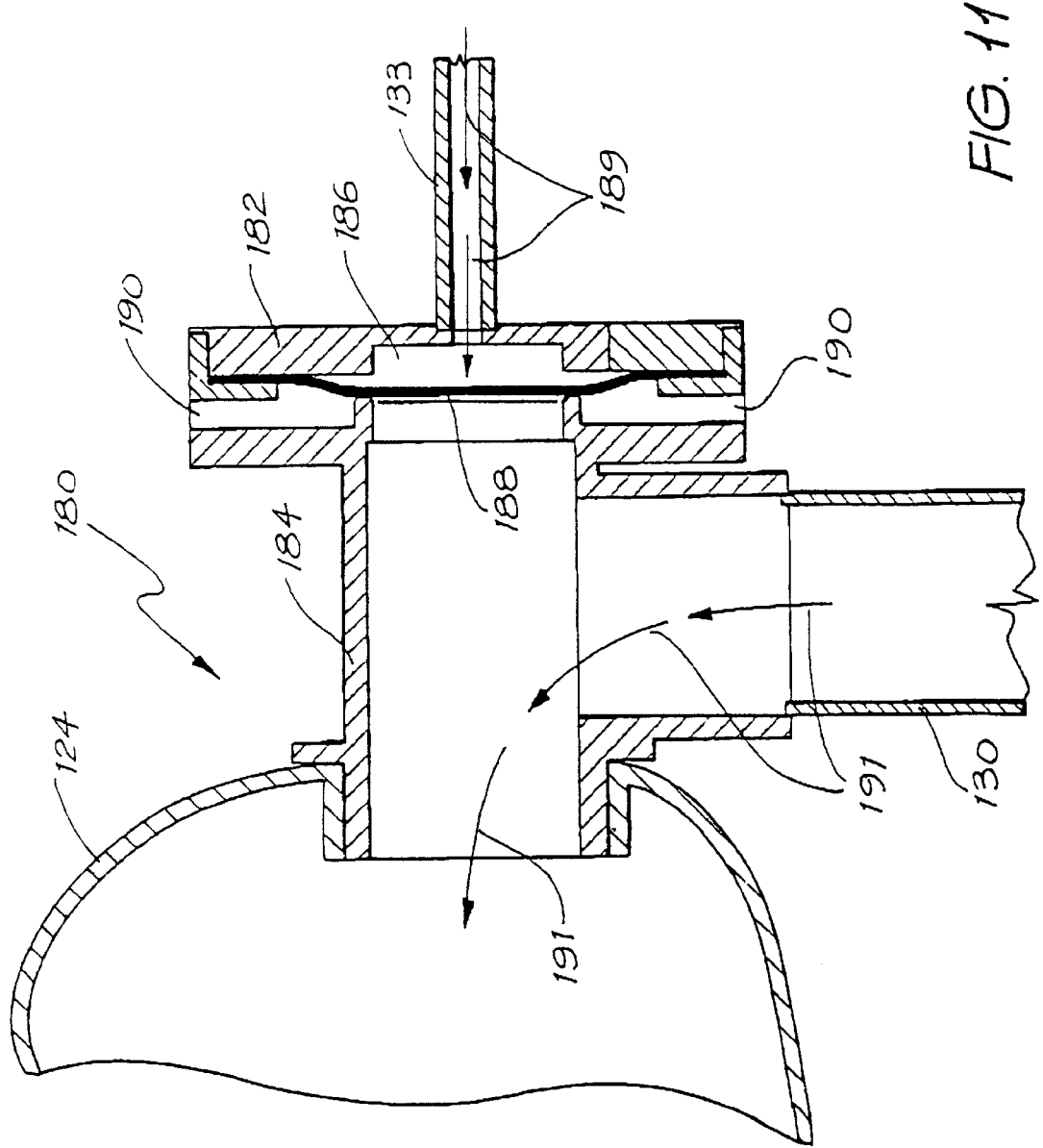
FIG. 11 is the exhaust servo valve of the embodiment of FIG. 7 during inhalation.
Figure 12:
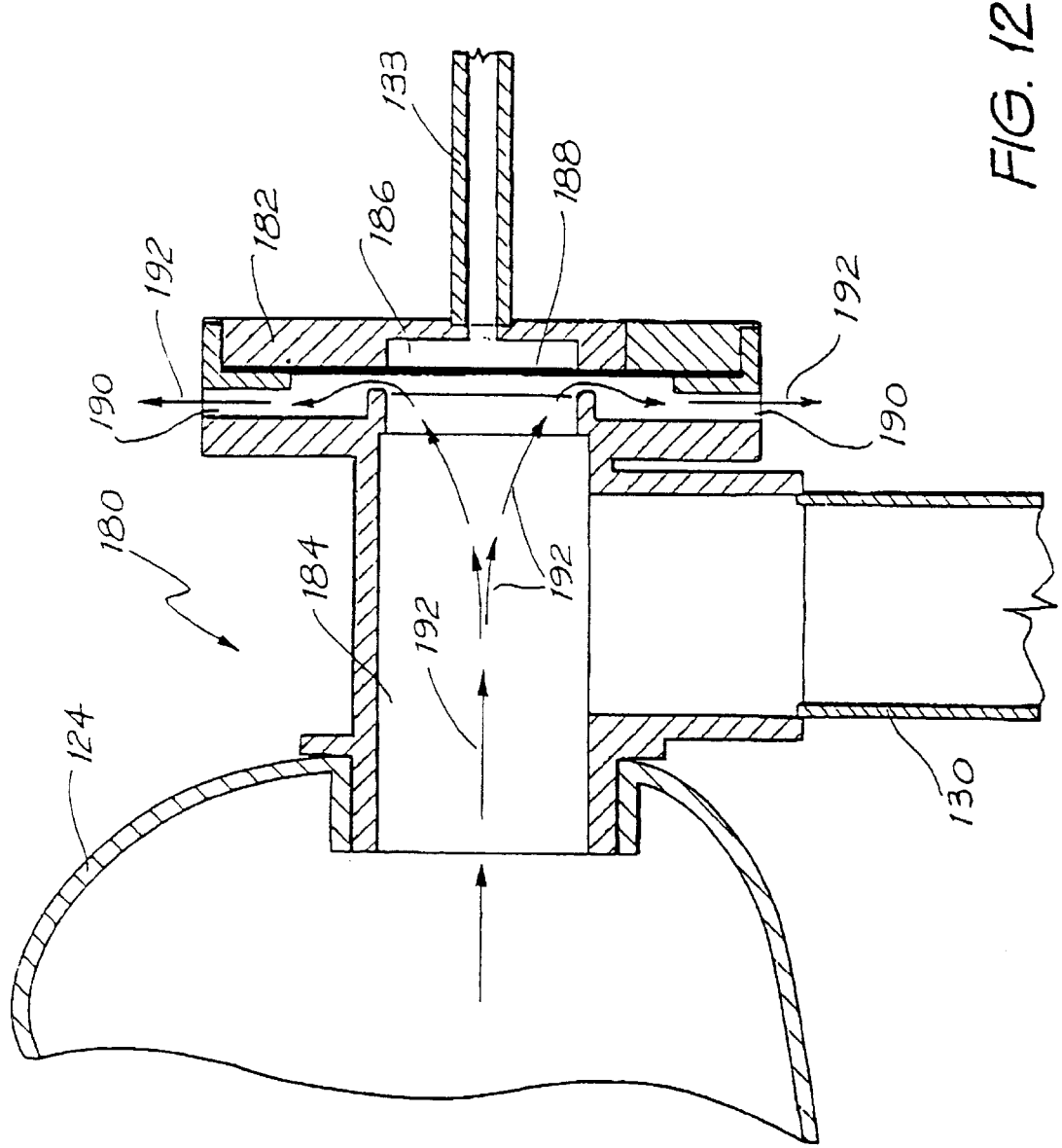
FIG. 12 is the exhaust servo valve of the embodiment of FIG. 7 during exhalation.

FIGS. 11 and 12 show the exhaust servo valve 180 which is interposed between the mask 124 and the mask supply tube 130. The valve 180 is also connected to servo valve supply tube 133. The valve 180 comprises a diaphragm body 182 and an outlet chamber 184. The diaphragm body 182 includes an exhaust control chamber 186 separated from the outlet chamber 184 by flexible exhaust control diaphragm 188. The chamber 186 is adapted to receive the tertiary air supply from the servo valve supply tube 133. The diaphragm body 182 also includes exhaust outlets 190 for venting releasing exhaled air in the outlet chamber 184 to atmosphere, as will be described below.

Figure 9:
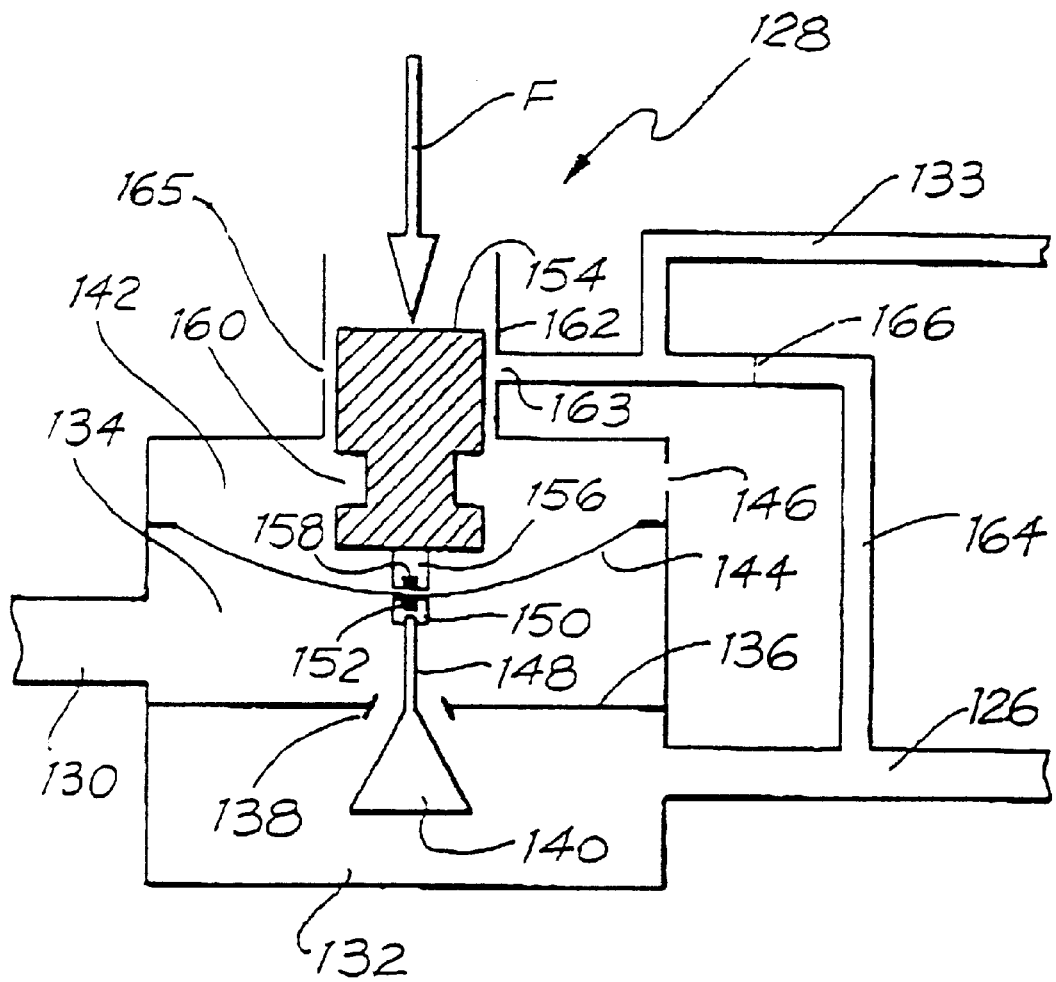
FIG. 9 is the main body of the embodiment of FIG. 8 during inhalation.

As shown in FIG. 9, on inhalation by the patient, the pressure of air within the outlet chamber 134 reduces instantaneously with the flow and no longer balances the downward force of the control valve member 154 causing it to fall in the direction of arrow F and deflect the diaphragm 144 downwards. This deflection displace the valve member 140 away from the opening 138 and allows air from the inlet chamber 132 to pass to the outlet chamber 134 and to the patient via the mask supply tube 130 and the mask 124.

FIG. 11 shows the exhaust servo valve 180 during inhalation. The tertiary air entering chamber 186 through the servo valve supply tube 133, as indicated by arrow 189, inflates and deflects the diaphragm 188 into blocking the exhaust outlets 190.

Accordingly, the air supplied to the mask 124 through the mask supply tube 130 is supplied to the patient, as indicated by arrows 191.

Figure 10:
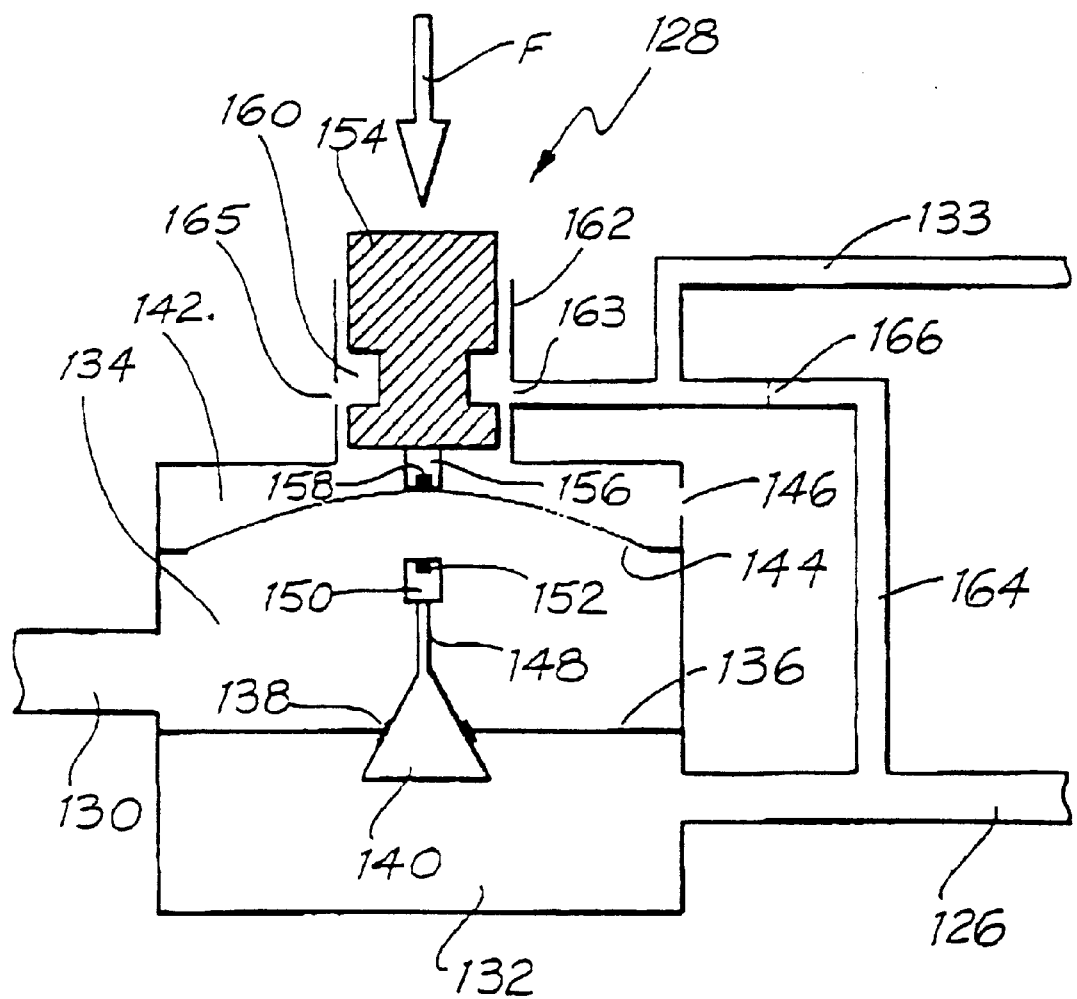
FIG. 10 is the main body of the embodiment of FIG. 9 during exhalation.

As shown in FIG. 10, on patient exhalation (expiration), the pressure within the outlet chamber 134 increases to a level which overcomes the downward force of the valve member 154 resulting in the diaphragm 144 deflecting upwardly and lifting the valve member 154 to a position where the groove 160 provides air communication between the inlet 163 and the outlet 165 thereby venting the branch delivery tube 164 and the servo valve supply tube 133 to atmosphere. Whilst the valve member 154 is in the raised position shown, the attractive force between the magnets 152 and 154 maintains the valve member 140 in a position closing the opening 138, as shown, thereby preventing a supply of air from the delivery tube 126 to the mask 124.

FIG. 12 shows the servo exhaust valve 180 during patient exhalation. As the air in the servo valve supply tube 133 is venting to atmosphere the membrane 188 will relax sufficiently for the pressure of the air exhausted by the patient to overcome the seal of the membrane 188 thereby opening the exhaust outlets 190 and allowing the passage of exhaled air to atmosphere, as indicated by arrows 192.

Figure 13:
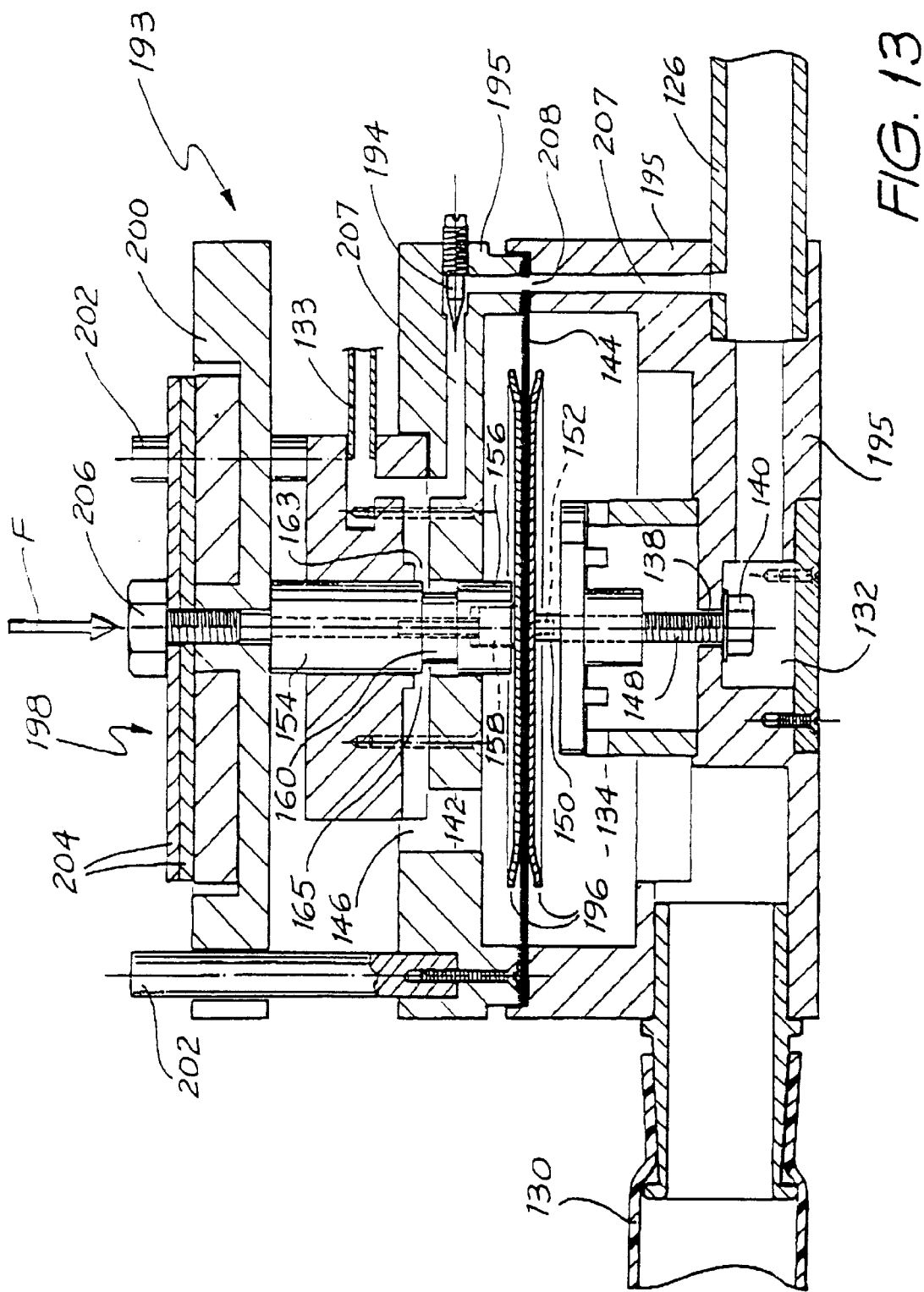
FIG. 13 is a cross-sectional view of the main body of a fifth embodiment of a delivery pressure controlling apparatus.

FIG. 13 shows a cross-sectional view of a main body 193 of a fifth embodiment which is, in essence, a practical construction of the main body 128 of the fourth embodiment. The fifth embodiment functions substantially identically to the fourth embodiment and like reference numerals to those used in FIGS. 8 to 10 will be used in relation to FIG. 13, except where indicated below.

Referring to FIG. 13, the flow restrictor 166 shown in FIGS. 7 to 12 is in the embodiment of FIG. 13, in the form of an adjustable needle valve 194 which is threadably received within multi-component plastic housing 195 of the main body 193. Also, the diaphragm 144 includes aluminum stiffening plates 196 either side thereof. The control valve member 154 is urged towards the diaphragm 144 by an adjustable weight assembly 198. The weighting assembly 198 includes a weight carriage 200 which is adapted for reciprocating vertical travel along three cylindrical guide members 202 (only two shown) and supports complementary shaped weights 204 which are held by retaining bolt 206. The branch delivery tube 164 shown in FIGS. 7 to 12 is, in the embodiment of FIG. 13, in the form of channel 207 machined into the housing 195 and which directs air through a hole 208 in diaphragm 144.

The operation of the fifth embodiment during a breathing cycle will now be described. During all phases of breathing the inlet chamber 132 of the main body 193 is supplied air at a pressure substantially above the maximum treatment pressure of the apparatus 120 (FIG. 14) and at a flow rate high enough to satisfy patient breathing requirements, for example about 90 cm $H_2O$ at a maximum flow rate of around 120 l/min. The air supply stalls when the valve member 140 closes the opening 138.

The valve member 154 is calibrated by adding the weights 204 until the valve member 154 is urged downwardly when the predetermined treatment pressure in the outlet chamber 134 falls below, for example, 10 cm $H_2O$. Depending on patient requirements, the treatment pressure can be set between about 4 cm $H_2O$ and 20 cm $H_2O$ by adding or removing the weights 204.

During inspiration, the pressure in the outlet chamber 134 falls below 10cm $H_2O$ and the valve member 154 is urged in the direction of arrow F thereby causing the plug valve member 140 to be urged away from opening 138 to allow air flow from inlet chamber 132 to outlet chamber 134 and so on to the delivery tube 130 and the mask 124 to the patient.

In this position, the valve member 154 blocks flow between the valve member housing inlet 163 and outlet 165. The air passing through the channel 207 is therefore diverted through the servo valve supply tube 133 to the exhaust control chamber 186 (see FIG. 12) of the mask outlet valve 180. The flow restrictor 166 is set to provide a pressure much greater than the treatment pressure which, in this example, results in the pressure in the supply tube 133 approaching the pressure of the primary air supply in the delivery tube 126. This pressure inflates the exhaust control diaphragm 188 to the position shown in FIG. 11 closing the exhaust ports 190. Accordingly, the air leaving the outlet chamber 130 is sent to the mask 124.

If the pressure supplied to the exhaust control chamber 186 is set above the treatment pressure, and if the patient pauses between inhalation or exhalation or vice versa, then the apparatus will remain in the "stalled" configuration represented by FIGS. 8 and 11.

If the pressure supplied to the exhaust control chamber 186 is set below the treatment pressure then the control diaphragm 188 will relax during a pause and allow some venting through the mask outlets 190.

During exhalation, the pressure in the outlet chamber 134 increases above the 10 cm $H_2O$ treatment pressure causing the control valve member 154 to rise until the groove 160 thereof provides air communication between the valve member housing inlet 163 and outlet 165. When this occurs, the air in supply line 133 vents to atmosphere through the outlet 165 and the diaphragm 188 relaxes to the position shown in FIG. 12 allowing the exhaled air to leave the mask 124 through the outlet 190.

The attraction between the magnets 152 and 158 maintains the valve member 140 in the closed position shown in FIG. 8. The primary air supply stalls whilst the opening 138 is closed by the valve member 140.

The primary air supply is throttled as it passes through the opening 138. As inhalation ends, the air flow rate and the pressure in the outlet chamber 134 on the underside of the diaphragm 144 increases above the treatment pressure of 10 cm $H_2O$ causing the diaphragm 144 to raise and lift the control valve member 154 until the equilibrium position schematically in FIG. 8 is reached.

In some CPAP apparatus air (or other breathable gas) is continuously supplied at a constant pressure to the patient. When exhaling the patient must overcome the pressure of the supplied gas to expel exhaled air and the supplied gas from the mask through a washout vent.

In bi-level CPAP treatment, patient breathing is monitored and the supply pressure is lowered during exhalation to reduce the effort in overcoming the pressurized supply to washout the exhaled air.

All the embodiments of the apparatus stop the supply of pressurized gas to the patient as soon as the patient exhalation initially overcomes the treatment pressure, thereby reducing the effort of further exhalation. Pressurized air supply resumes when the patient inhales.

The third embodiment of this apparatus can also be configured to provide bi-level CPAP treatment as previously explained.

Figure 14:
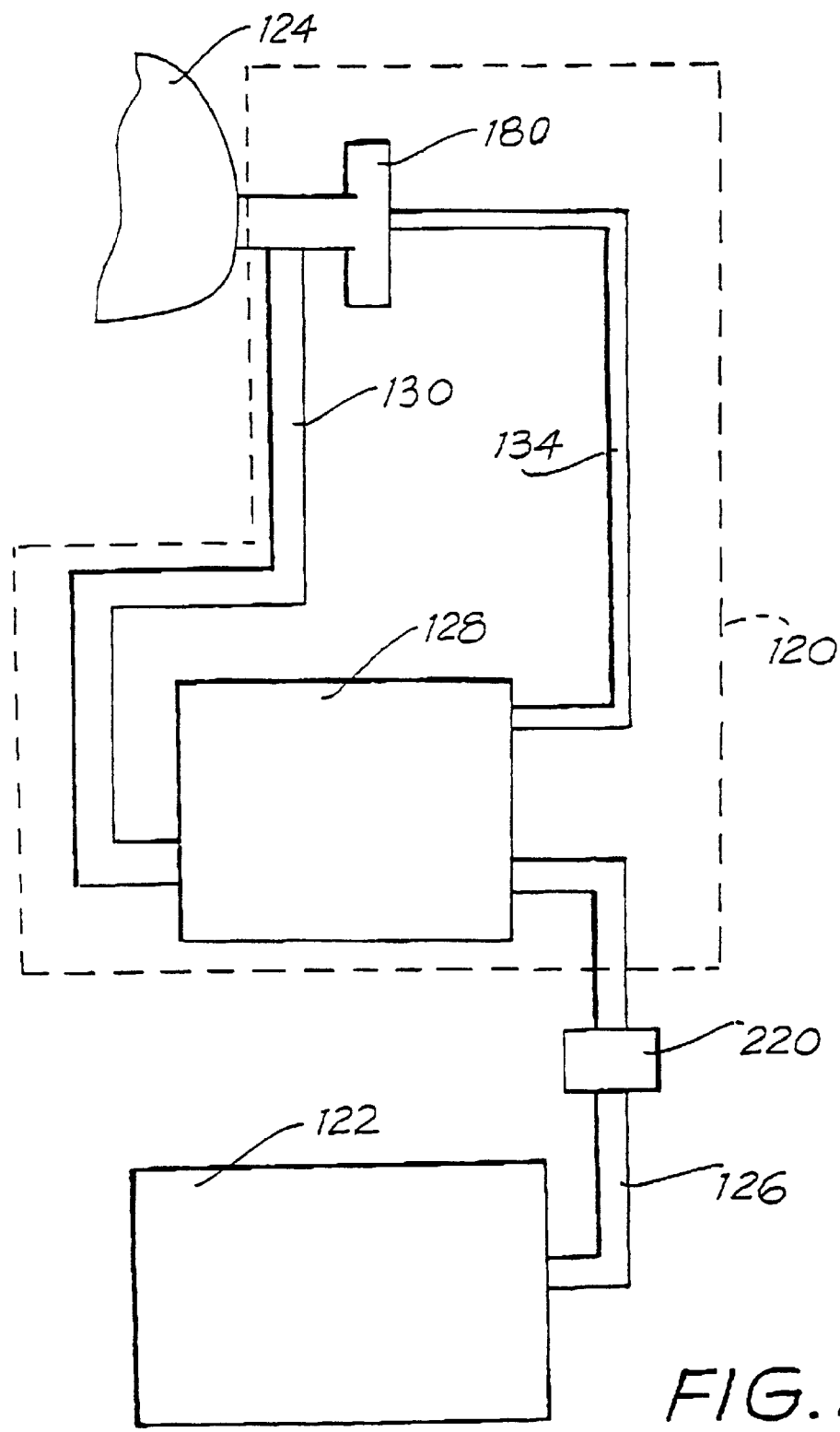
FIG. 14 is a schematic view of a fifth embodiment of a delivery pressure apparatus incorporated into a CPAP system.

FIG. 14 shows a general arrangement of a sixth embodiment similar to the fourth and fifth embodiments which includes a gas supply accumulator or reservoir 220 interposed between the gas supply 122 and the apparatus 120. The accumulator 220 can be in the form of a bellows or gas cylinder or the like and is used to provide a buffer volume of gas to ensure the demands of abnormally large breaths are met. This allows a smaller and less expensive pump or like gas supply source to be used which is optimised to supply a "normal" volume of gas. The accumulator also dampens or flattens the pressure pulses associated with positive displacement pump.

Although the invention has been described with reference to preferred embodiments, it will be appreciated by those skilled in the art that the invention may be embodied in many other forms.

What is claimed is:

1. A pressure control apparatus for CPAP treatment or assisted respiration, said apparatus comprising:
   an inlet chamber for connection to a primary supply of air or other breathable gas at a pressure at or above a minimum treatment pressure;
   an outlet chamber for communication with a mask;
   a diaphragm for communication with a portion of said outlet chamber;
   means to provide a predetermined force to said diaphragm;
   a first valve means operable to open a flow path between said outlet chamber and said inlet chamber in response to deflection of said diaphragm in a first direction; and
   a second valve means operable to provide an exhaust path from said outlet chamber to atmosphere in response to deflection of said diaphragm in a second direction opposite to said first direction;
      wherein when the pressure of gas in said outlet chamber produces a force on the diaphragm below said predetermined force the force differential on said diaphragm causes it to deflect in said first direction and cause said first valve means to open and to case an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;
      wherein said reference force providing means comprises a predetermined mass adapted to urge said diaphragm in said first direction;
      wherein said apparatus includes a control valve member slidable within a control valve member housing; and
      wherein said apparatus includes weights adapted to be added to said control valve member to vary said mass.

2. A pressure control apparatus for CPAP treatment or assisted respiration, said apparatus comprising:
   an inlet chamber for connection to a primary supply of air or other breathable gas at a pressure at or above a minimum treatment pressure;
   an outlet chamber for communication with a mask;
   a diaphragm for communication with a portion of said outlet chamber;
   means to provide a predetermined force to said diaphragm;
   a first valve means operable to open a flow path between said outlet chamber and said inlet chamber in response to deflection of said diaphragm in a first direction; and
   a second valve means operable to provide an exhaust path from said outlet chamber to atmosphere in response to deflection of said diaphragm in a second direction opposite to said first direction;
      wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;
      wherein said reference force providing means comprises a predetermined mass adapted to urge said diaphragm in said first direction;
      wherein said apparatus includes a control valve member slidable within a control valve member housing; and
      wherein said control valve member housing includes a control valve inlet in communication with a secondary supply gas below said maximum treatment pressure.

3. An apparatus according to claim 2, wherein said secondary supply of gas is provided by passing a portion of the primary supply through a pressure reducing valve operable to reduce the pressure of the secondary gas supply to said treatment pressure.

4. An apparatus according to claim 3, wherein said pressure reducing valve is adapted to provide fixed or variable pressure reduction.

5. A pressure control apparatus for CPAP treatment or assisted respiration, said apparatus comprising:
   an inlet chamber for connection to a primary supply of air or other breathable gas at a pressure at or above a minimum treatment pressure;
   an outlet chamber for communication with a mask;
   a diaphragm for communication with a portion of said outlet chamber;
   means to provide a predetermined force to said diaphragm;
   a first valve means operable to open a flow path between said outlet chamber and said inlet chamber in response to deflection of said diaphragm in a first direction; and
   a second valve means operable to provide an exhaust path from said outlet chamber to atmosphere in response to deflection of said diaphragm in a second direction opposite to said first direction;
      wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;

wherein said reference force providing means comprises a predetermined mass adapted to urge said diaphragm in said first direction;

wherein said apparatus includes a control valve member slidable within a control valve member housing; and wherein said control valve member housing includes a control valve outlet to atmosphere.

6. An apparatus according to claim 5, wherein said control valve member includes a groove adapted to provide a flow path between said control valve inlet and said control valve outlet when urged in said second direction.

7. A pressure control apparatus for CPAP treatment or assisted respiration, said apparatus comprising;

an inlet chamber for connection to a primary supply of air or other breathable gas at a pressure at or above a minimum treatment pressure;

an outlet chamber for communication with a mask;

a diaphragm for communication with a portion of said outlet chamber;

means to provide a predetermined force to said diaphragm;

a first valve means operable to open a flow path between said outlet chamber and said inlet chamber in response to deflection of said diaphragm in a first direction; and a second valve means operable to provide an exhaust path from said outlet chamber to atmosphere in response to deflection of said diaphragm in a second direction opposite to said first direction;

wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;

wherein said reference force providing means comprises a predetermined mass adapted to urge said diaphragm in said first direction;

wherein said apparatus includes a control valve member slidable within a control valve member housing; and wherein said control valve member includes a magnet disposed on the control valve side of the diaphragm.

8. A pressure control apparatus for CPAP treatment or assisted respiration, said apparatus comprising:

an inlet chamber for connection to a primary supply of air or other breathable gas at a pressure at or above a minimum treatment pressure;

an outlet chamber for communication with a mask;

a diaphragm for communication with a portion of said outlet chamber;

means to provide a predetermined force to said diaphragm;

a first valve means operable to open a flow path between said outlet chamber and said inlet chamber in response to deflection of said diaphragm in a first direction; and a second valve means operable to provide an exhaust path from said outlet chamber to atmosphere in response to deflection of said diaphragm in a second direction opposite to said first direction;

wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;

wherein said predetermined force providing means comprises a spring adapted to urge said diaphragm in said first direction;

wherein varying the resilience of the spring varies said predetermined force and said treatment pressure; and wherein said first valve means is a plug valve member having an elongate tail terminating in a magnet disposed on the outlet chamber side of the diaphragm.

9. An apparatus according to claim 8, wherein said plug valve member magnet and said control valve member magnet are configured to attract each other.

10. A pressure control apparatus for CPAP treatment or assisted respiration, said apparatus comprising:

an inlet chamber for connection to a primary supply of air or other breathable gas at a pressure at or above a minimum treatment pressure;

an outlet chamber for communication with a mask;

a diaphragm for communication with a portion of said outlet chamber;

means to provide a predetermined force to said diaphragm;

a first valve means operable to open a flow path between said outlet chamber and said inlet chamber in response to deflection of said diaphragm in a first direction; and a second valve means operable to provide an exhaust path from said outlet chamber to atmosphere in response to deflection of said diaphragm in a second direction opposite to said first direction;

wherein when the pressure of gas in said outlet chamber produces a force on the diaphragm below said predetermined force the force differential on said diaphragm causes it to deflect in said first direction and cause said first valve means to open and to cause an equilibrating flow of gas from said inlet chamber, and further wherein when the pressure of gas in said outlet chamber produces a force on the diaphragm above said predetermined force the force differential on said diaphragm causes it to deflect in said second direction and cause said second valve means to open;

wherein said reference force providing means comprises a predetermined mass adapted to urge said diaphragm in said first direction; and wherein said apparatus includes an exhaust chamber in communication with said outlet chamber including at least one exhaust port, and an exhaust control chamber in communication with a tertiary supply of gas above said treatment pressure and including an exhaust port control diaphragm adapted to open or close said exhaust port(s) to atmosphere wherein when said second valve means is closed said tertiary air supply deflects said exhaust port control diaphragm into closing said exhaust port and further wherein opening of the second valve means is open said exhaust control chamber vents to atmosphere thereby relaxing said exhaust port control diaphragm and opening said exhaust port to provide an exhaust path from said outlet chamber to said exhaust chamber to atmosphere.

11. An apparatus according to claim 10, wherein said tertiary gas supply is provided by passing a portion of said secondary gas supply through a flow restrictor.

12. An apparatus according to claim 10, wherein deflection of the diaphragm in the first direction causes the diaphragm to abut and thereafter displace the first plug valve member to an open position allowing communication between the inlet chamber and the outlet chamber and the control valve member to be urged by said mass to a first position blocking communication between the control valve member housing inlet and outlet and further wherein deflection of the diaphragm in the second direction causes the diaphragm to abut and thereafter displace the control valve member to a second position aligning said groove with the control valve member inlet and outlet thereby providing communication therebetween to vent said exhaust control chamber to atmosphere and open said exhaust port(s), whereby when said control valve member is in the second position the attraction between said magnets urges said first plug valve member to a closed portion.

13. An apparatus according to claim 10, wherein said exhaust chamber, said exhaust control chamber and said exhaust port control diaphragm are incorporated into a mask assembly attached to, or integral with, said mask and further, wherein said exhaust control chamber communicates with said main body by an exhaust servo valve supply tube.

* * * * *